(12) United States Patent
Straub et al.

(10) Patent No.: US 6,743,798 B1
(45) Date of Patent: Jun. 1, 2004

(54) SUBSTITUTED PYRAZOLE DERIVATIVES CONDENSED WITH SIX-MEMBERED HETEROCYCLIC RINGS

(75) Inventors: Alexander Straub, Wuppertal (DE); Achim Feurer, Odenthal (DE); Cristina Alonso-Alija, Haan (DE); Johannes-Peter Stasch, Solingen (DE); Elisabeth Perzborn, Wuppertal (DE); Joachim Hütter, Wuppertal (DE); Klaus Dembowsky, Boston, MA (US); Elke Stahl, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/744,830

(22) PCT Filed: Jul. 16, 1999

(86) PCT No.: PCT/EP99/05074
§ 371 (c)(1),
(2), (4) Date: Apr. 11, 2001

(87) PCT Pub. No.: WO00/06569
PCT Pub. Date: Feb. 10, 2000

(30) Foreign Application Priority Data

Jul. 29, 1998 (DE) .......................... 198 34 044

(51) Int. Cl.$^7$ ............... C07D 403/04; C07D 403/14; A61K 31/52; A61K 31/525

(52) U.S. Cl. .......... 514/256; 514/269; 514/272; 514/274; 514/275; 514/263.2; 514/252.16; 514/252.15; 514/252.14; 514/235.8; 514/228.5; 514/227.8; 514/226.8; 514/218; 514/217.06; 514/212.02; 514/85; 514/81; 544/333; 544/6; 544/57; 544/58.6; 544/58.2; 544/60; 544/122; 544/123; 544/118; 544/157; 544/243; 544/244; 544/264; 544/310; 544/316; 544/324; 544/328; 544/331; 540/601; 540/544; 540/575; 540/553

(58) Field of Search ................. 544/319, 122, 544/327, 298, 328, 333, 60, 362, 335, 243, 262, 58.2, 310, 316, 324, 331, 6, 57, 58.6, 123, 118, 157, 244, 264; 514/117, 269, 235.8, 252.18, 227.8, 256, 266, 263.2, 81, 85, 212.02, 217.06, 218, 226.8, 228.5, 252.14, 252.15, 252.16, 272, 274, 275; 540/601, 544, 575, 553

(56) References Cited

U.S. PATENT DOCUMENTS

| 4,500,525 A | 2/1985 | Winters et al. ............. 514/210 |
| 5,574,168 A | 11/1996 | Kuo et al. ............... 548/360.5 |

FOREIGN PATENT DOCUMENTS

| EP | 0086422 | 8/1983 | ......... C07D/471/04 |
| EP | 0667345 | 8/1995 | ......... C07D/405/04 |
| WO | 9816507 | 4/1998 | |
| WO | 09823619 | 6/1998 | ......... C07D/487/04 |

OTHER PUBLICATIONS

Beavo, J. A., and Reifsnyder, D. H., "Primary Sequence of Cyclic Nucleotide Phosphodiesterase Isozymes and the Design of Selective Inhibitors", TIPS, 11: 150–155 (Apr. 1990).

Borsche, W., and Manteuffel, R., "Uber die Kondensation von Saureestern mit aliphatischen Nitrilen", Liebigs, Ann., 512:97–112 (1934).

*Primary Examiner*—John M. Ford

(57) ABSTRACT

The present invention relates to novel substituted pyrazole derivatives of the general formula (I)

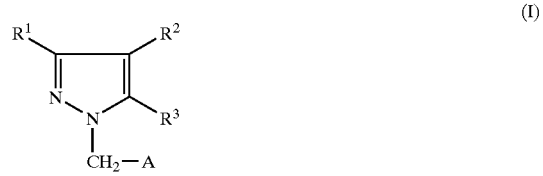

in which $R^1$, $R^2$, $R^3$ and A are each as defined, and to processes for their preparation and to their use as medicaments, in particular as medicaments for the treatment of cardiovascular disorders.

8 Claims, 2 Drawing Sheets

Stimulation of soluble guanylate cyclase by 3-(4,6-diamino-5-N-morpholino-2-pyrimidinyl)-1-(2-fluorobenzyl)-1H-pyrazolo[3,4-b]-pyridine (example 16) in the presence of various NO-concentrations.

Effect of 3-(4,6-diamino-5-N-morpholino-2-pyrimidinyl)-1-(2-fluorobenzyl)-1H-pyrazolo[3,4-b]-pyridine (example 16) on the mean blood pressure of conscious, spontaneously hypertensive rats.

SUBSTITUTED PYRAZOLE DERIVATIVES CONDENSED WITH SIX-MEMBERED HETEROCYCLIC RINGS

The present invention relates to novel substituted pyrazole derivatives, to processes for their preparation and to their use as medicaments, in particular as medicaments for the treatment of cardiovascular disorders according to claims 1 to 10.

It is already known that 1-benzyl-3-(substituted heteroaryl)-fused pyrazole derivatives inhibit thromocyte aggregation (cf. EP 667 345 A1).

WO 98/16223 discloses the use of 1-benzyl-3-(substituted hetaryl)-fused pyrazole derivatives for the treatment of specific disorders of the cardiovascular system and the central nervous system.

WO 98/16507 discloses heterocyclylmethyl-substituted pyrazole derivatives and their use in the treatment of cardiovascular disorders.

WO 98/23619 likewise discloses substituted pyrazole derivatives for the treatment of cardiovascular disorders.

Figure 1:
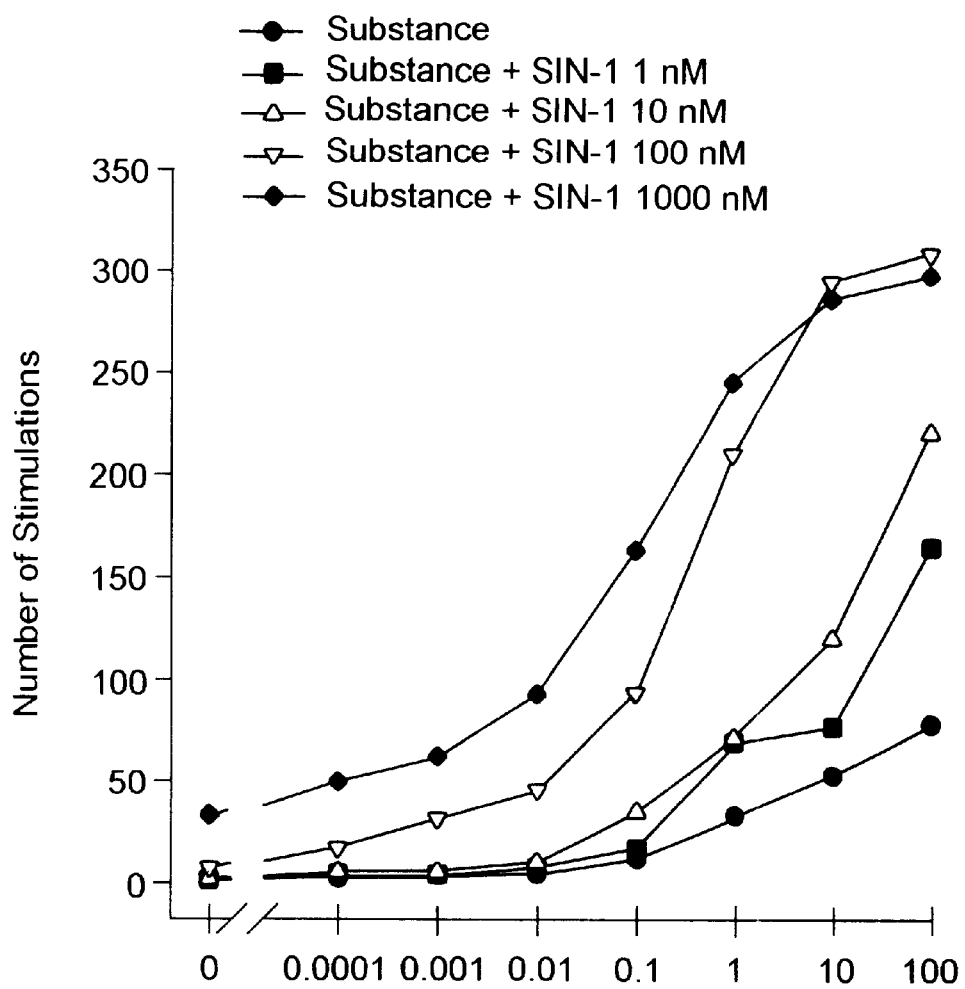
FIG. 1 shows stimulation of soluble guanylate cyclase by 3-(4,6-diamino-5-N-morpholino-2-pyrimidinyl)-1-(2-fluorobenzyl)-1H-pyrazolo[3,4-b]-pyridine (example 16) in the presence of various NO-concentrations.

The present invention relates to substituted pyrazole derivatives of the general formula (I)

in which
  $R^1$ represents a saturated or aromatic 5- or 6-membered heterocycle having up to 3 heteroatoms from the group consisting of S, N and O, which may be attached via a nitrogen atom,
  and which is optionally substituted up to 2 times by identical or different radicals from the group (i) consisting of
    hydrogen, amino, azido, formyl, mercaptyl, carboxyl, hydroxyl, straight-chain or branched acyl, alkoxy, alkylthio or alkoxy-carbonyl having in each case up to 6 carbon atoms, nitro, cyano, halogen, phenol or straight-chain or branched alkyl having up to 6 carbon atoms which for its part may be substituted by hydroxyl, amino, azido, carboxyl, straight-chain or branched acyl, alkoxy, alkoxycarbonyl or acylamino having in each case up to 5 carbon atoms or by a radical of the formula $-OR^4$ in which
  $R^4$ represents straight-chain or branched acyl having up to 5 carbon atoms
  and/or is substituted by a radical of the formula

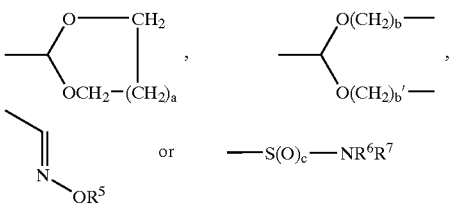

or $-S(O)_c-NR^6R^7$ in which
  a, b and b' are identical or different and each represents a number 0, 1, 2 or 3,
  $R^5$ is hydrogen or straight-chain or branched alkyl having up to 4 carbon atoms,
  c is a number 1 or 2 and
  $R^6$ and $R^7$ are identical or different and each represents hydrogen or straight-chain or branched alkyl having up to 10 carbon atoms which is optionally substituted by cycloalkyl having 3 to 8 carbon atoms or by aryl having 6 to 10 carbon atoms which for its part may be substituted by halogen,
    or
    represents aryl having 6 to 10 carbon atoms which is optionally substituted by halogen,
    or
    represents cycloalkyl having 3 to 7 carbon atoms,
    or
  $R^6$ and $R^7$ together with the nitrogen atom form a 5- to 7-membered saturated heterocycle which may optionally contain a further oxygen atom or a radical $-NR^8$
  in which
    $R^8$ represents hydrogen, straight-chain or branched alkyl having up to 4 carbon atoms or a radical of the formula

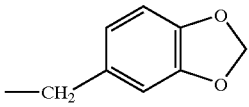

or benzyl or phenyl where the ring systems are optionally substituted by halogen,
and which is substituted by at least one radical from the group (ii) consisting of
  a 3- to 8-membered ring which may be saturated, unsaturated or partially unsaturated, contains 1 to 4 heteroatoms from the group consisting of N, O, S, SO, $SO_2$ and which may also be attached via N, imidazolyl, imidazolinyl, imidazolidinyl, morpholinyl, piperidinyl, piperazinyl, pyrrolidinyl, triazolyl, pyrrolyl, thiomorpholinyl, S-oxothiomorpholinyl and S,S-dioxothiomorpholinyl being particularly preferred, and which is optionally mono- or polysubstituted by a 5- or 6-membered ring which contains two oxygen atoms as ring members and forms a bicyclic unit or a spiro unit with the 3- to 8-membered ring, and/or by hydroxyl, cyano, straight-chain or branched alkyl, acyl or alkoxycarbonyl having in each case up to 6 carbon atoms, where alkyl, acyl and alkoxycarbonyl may be substituted by hydroxyl, amino, halogen, carboxyl, straight-chain or branched acyl, alkoxy, alkoxycarbonyl or acylamino having in each case up to 5 carbon atoms, and an aryl ring having 6 to 10 carbon atoms which is substituted by straight-chain or branched alkyl having up to 4 carbon atoms, and $(C_2-C_{10})$alkenyl, $(C_2-C_{10})$alkinyl, $(C_7-C_{20})$alkyl, which is optionally substituted by aryl, heteroaryl, halogen, cyano, dialkylamino, cycloalkyl, alkylamine, hydroxyl, amino, azido, carboxyl, straight-chain or branched acyl, alkoxy, alkoxycarbonyl or acylamino having in each case up to 5 carbon atoms or by a radical of the formula $—OR^4$ in which $R^4$ represents straight-chain or branched acyl having up to 5 carbon atoms and $(C_1-C_6)$alkyl which is substituted 1- to 3 times by aryl, heteroaryl, halogen(s), cyano, dialkylamino, alkylamino or cycloalkyl and acyl, which is substituted by halogen(s), particularly preferably by fluorine, or by acyloxy, arylthio or heteroarylthio, and —NO or radicals of the formulae $—SO_3H$ and $—S(O)_d R^9$, in which d represents a number 1 or 2, $R^9$ represents straight-chain or branched alkyl having 1 to 10 carbon atoms, cycloalkyl having 3 to 8 carbon atoms, aryl having 6 to 10 carbon atoms or a saturated or unsaturated 5- to 6-membered heterocycle having up to 3 heteroatoms from the group consisting of S, N and O, where the ring systems may optionally be substituted by halogen or by straight-chain or branched alkyl or alkoxy having in each case up to 4 carbon atoms, and a radical of the formula $PO(OR^{10})(OR^{11})$ in which $R^{10}$ and $R^{11}$ are identical or different and each represents hydrogen, straight-chain or branched alkyl having up to 8 carbon atoms or cycloalkyl having 3 to 8 carbon atoms, aryl having 6 to 10 carbon atoms or benzyl, and oxycycloalkyl having 3 to 8 ring members or radicals of the formulae $—CON=C(NH_2)_2$, $—C=NH(NH_2)$, $—NH—C(=NH)NH_2$ or $(CO)_eNR^{12}R^{13}$ in which e represents a number 0 or 1, $R^{12}$ and $R^{13}$ are identical or different and each represents hydrogen, straight-chain or branched alkyl having up to 14 carbon atoms or cycloalkyl having 3 to 14 carbon atoms, aryl having 6 to 10 carbon atoms or a saturated or unsaturated 3- to 10-membered ring having up to 5 heteroatoms from the group consisting of N, O, S, where the abovementioned radicals may optionally be substituted by aryl having 6 to 10 carbon atoms, heterocyclyl, cycloalkyl having 3 to 7 carbon atoms, hydroxyl, amino or straight-chain or branched alkoxy, acyl or alkoxycarbonyl having in each case up to 6 carbon atoms, and, in the case that e=1, $R^{12}$ and $R^{13}$, together with the nitrogen atom to which they are attached, may also form a 5- or 6-membered ring having up to 3 heteroatoms from the group consisting of N, O, S, which may optionally be substituted up to 3 times by hydroxyl, alkoxy or alkyl having in each case up to 8 carbon atoms, and, in the case that e=0, $R^{12}$ and $R^{13}$ may also represent straight-chain, branched or cyclic acyl having up to 14 carbon atoms, hydroxyalkyl, straight-chain or branched alkoxycarbonyl or acyloxyalkyl having in each case up to 6 carbon atoms, or a radical of the formula $—SO_2R^{14}$ in which $R^{14}$ represents straight-chain or branched alkyl having up to 4 carbon atoms, and/or $R^{12}$ and $R^{13}$ also represent radicals of the formulae

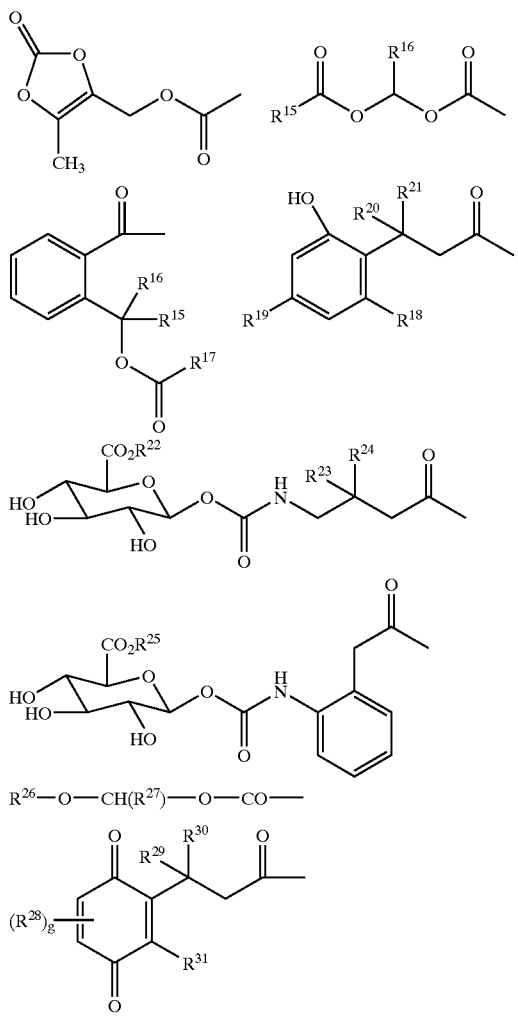

in which $R^{15}-R^{16}$ and $R^{18}-R^{31}$ are identical or different and each represents hydrogen or straight-chain or branched alkyl having up to 4 carbon atoms, g represents a number 0, 1 or 2, and $R^{17}$ represents phenyl, straight-chain or branched alkyl having up to 6 carbon atoms or cycloalkyl having 3 to 8 carbon atoms, with the proviso that, if e=0, $R^{12}$ and $R^{13}$ do not simultaneously represent hydrogen, or $R^1$ represents a purine radical which may optionally be substituted up to three times by halogen, azido, cyano, hydroxyl, amino, monoalkylamino having up to 5 carbon atoms, dialkylamino having in each case up to 5 carbon atoms, alkyl having up to 5 carbon atoms and/or alkoxy having up to 5 carbon atoms, $R^2$ and $R^3$, together with the double bond, form a 6-membered saturated or aromatic heterocycle having up to 3 heteroatoms from the group consisting of N, S and O, which is optionally substituted up to three times by identical or different substituents from the group consisting of formyl, carboxyl, hydroxyl, mercaptyl, straight-chain or branched acyl, alkylthio or alkoxycarbonyl having in each case up to 6 carbon atoms, nitro, cyano, halogen or straight-chain or branched alkyl or alkoxy having in each case up to 6 carbon atoms which for its part may be substituted by hydroxyl, amino, carboxyl, straight-chain or branched acyl, alkoxy or alkoxycarbonyl having in each case up to 5 carbon atoms, and/or which is optionally substituted by a group of the formula —$NR^{32}R^{33}$ in which $R^{32}$ and $R^{33}$ are identical or different and each represents hydrogen or straight-chain or branched alkyl having up to 6 carbon atoms, or $R^{32}$ represents hydrogen and $R^{33}$ represents acyl, and/or which is optionally substituted by phenyl which for its part may be substituted up to 2 times by identical or different substituents from the group consisting of halogen and straight-chain or branched alkyl or alkoxy having in each case up to 6 carbon atoms, and/or which is optionally substituted by a group of the formula

—N=CH—$NR^{34}R^{35}$ in which $R^{34}$ and $R^{35}$ are identical or different and each represents hydrogen, phenyl or straight-chain or branched alkyl having up to 6 carbon atoms, A represents a 5- or 6-membered aromatic or saturated heterocycle having up to 3 heteroatoms from the group consisting of S, N and O or represents phenyl, which are optionally substituted up to 3 times by identical or different substituents from the group consisting of amino, mercaptyl, hydroxyl, formyl, carboxyl, straight-chain or branched acyl, alkylthio, alkyloxyacyl, alkoxy or alkoxycarbonyl having in each case up to 6 carbon atoms, nitro, cyano, trifluoromethyl, azido, halogen, phenyl or straight-chain or branched alkyl having up to 6 carbon atoms which for its part may be substituted by hydroxyl, carboxyl, straight-chain or branched acyl, alkoxy or alkoxycarbonyl having in each case up to 5 carbon atoms, and/or is substituted by a group of the formula —$(CO)_h$—$NR^{36}R^{37}$ in which h represents a number 0 or 1, $R^{36}$ and $R^{37}$ are identical or different and each represents hydrogen, phenyl, benzyl or straight-chain or branched alkyl or acyl having in each case up to 5 carbon atoms, and their isomeric forms and salts.

Preference according to the invention is given to compounds of the general formula (I) in which $R^1$ represents a saturated or aromatic 6-membered heterocycle having up to 3 heteroatoms from the group consisting of S, N and O, which may be attached via a nitrogen atom, and which is optionally substituted up to 2 times by identical or different radicals from the group (i) consisting of hydrogen, amino, azido, formyl, mercaptyl, carboxyl, hydroxyl, straight-chain or branched acyl, alkoxy, alkylthio or alkoxy-carbonyl having in each case up to 6 carbon atoms, nitro, cyano, halogen, phenyl or straight-chain or branched alkyl having up to 6 carbon atoms which for its part may be substituted by hydroxyl, amino, azido, carboxyl, straight-chain or branched acyl, alkoxy, alkoxycarbonyl or acylamino having in each case up to 5 carbon atoms or by a radical of the formula —$OR^4$ in which $R^4$ represents straight-chain or branched acyl having up to 5 carbon atoms and/or is substituted by a radical of the formula

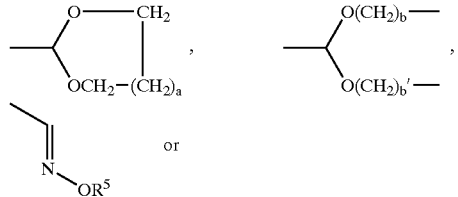

in which a, b and b' are identical or different and each represents a number 0, 1, 2 or 3, $R^5$ is hydrogen or straight-chain or branched alkyl having up to 4 carbon atoms, and which is substituted by at least one radical from the group (ii) consisting of a 3- to 8-membered ring which may be saturated, unsaturated or partially unsaturated, contains 1 to 4 heteroatoms from the group consisting of N, O, S, SO, $SO_2$ and which may also be attached via N, imidazolyl, imidazolinyl, imidazolidinyl, morpholinyl, piperidinyl, piperazinyl, pyrrolidine, triazolyl, pyrrolyl, thiomorpholinyl, S-oxothiomorpholinyl and S,S-dioxothiomorpholinyl being particularly preferred, and which is optionally mono- or polysubstituted by a 5- or 6-membered ring which contains two oxygen atoms as ring members and forms a bicyclic unit or a spiro unit with the 3- to 8-membered ring, and/or by hydroxyl, cyano, straight-chain or branched alkyl, acyl or alkoxycarbonyl having in each case up to 6 carbon atoms, where alkyl, acyl and alkoxycarbonyl may be substituted by hydroxyl, amino, halogen, carboxyl, straight-chain or branched acyl, alkoxy, alkoxycarbonyl or acylamino having in each case up to 5 carbon atoms, and an aryl ring having 6 to 10 carbon atoms which is substituted by straight-chain or branched alkyl having up to 4 carbon atoms, and
($C_2$–$C_{10}$)alkenyl, ($C_2$–$C_{10}$)alkinyl, ($C_7$–$C_{20}$)alkyl, which is optionally substituted by aryl, heteroaryl, halogen, cyano, dialkylamino, cycloalkyl, alkylamine, hydroxyl, amino, azido, carboxyl, straight-chain or branched acyl, alkoxy, alkoxycarbonyl or acylamino having in each case up to 5 carbon atoms or by a radical of the formula —$OR^4$
in which
$R^4$ represents straight-chain or branched acyl having up to 5 carbon atoms
and
($C_1$–$C_6$)alkyl which is substituted 1- to 3 times by aryl, heteroaryl, halogen(s), cyano, dialkylamino, alkylamino or cycloalkyl
and
acyl, which is substituted by halogen(s), particularly preferably by fluorine, or by acyloxy, arylthio or heteroarylthio,
and
—NO or radicals of the formulae —$SO_3H$ and —$S(O)_dR^9$,
in which
d represents a number 1 or 2,
$R^9$ represents straight-chain or branched alkyl having 1 to 10 carbon atoms, cycloalkyl having 3 to 8 carbon atoms, aryl having 6 to 10 carbon atoms or a saturated or unsaturated 5- to 6-membered heterocycle having up to 3 heteroatoms from the group consisting of S, N and O, where the ring systems may optionally be substituted by halogen or by straight-chain or branched alkyl or alkoxy having in each case up to 4 carbon atoms,
and
a radical of the formula $PO(OR^{10})(OR^{11})$
in which
$R^{10}$ and $R^{11}$ are identical or different and each represents hydrogen, straight-chain or branched alkyl having up to 8 carbon atoms or cycloalkyl having 3 to 8 carbon atoms, aryl having 6 to 10 carbon atoms or benzyl,
and
oxycycloalkyl having 3 to 8 ring members or radicals of the formulae —$CON=C(NH_2)_2$, —$C=NH(NH_2)$, —$NH$—$C(=NH)NH_2$ or $(CO)_eNR^{12}R^{13}$
in which
e represents a number 0 or 1,
$R^{12}$ and $R^{13}$ are identical or different and each represents hydrogen, straight-chain or branched alkyl having up to 14 carbon atoms or cycloalkyl having 3 to 14 carbon atoms, aryl having 6 to 10 carbon atoms or a saturated or unsaturated 3- to 10-membered ring having up to 5 heteroatoms from the group consisting of N, O, S, where the abovementioned radicals may optionally be substituted by aryl having 6 to 10 carbon atoms, heterocyclyl, cycloalkyl having 3 to 7 carbon atoms, hydroxyl, amino or straight-chain or branched alkoxy, acyl or alkoxycarbonyl having in each case up to 6 carbon atoms,
and, in the case that e=1,
$R^{12}$ and $R^{13}$, together with the nitrogen atom to which they are attached, may also form a 5- or 6-membered ring having up to 3 heteroatoms from the group consisting of N, O, S, which may optionally substituted up to 3 times by hydroxyl, alkoxy or alkyl having in each case up to 8 carbon atoms,
and, in the case that e=0,
$R^{12}$ and $R^{13}$ may also represent straight-chain, branched or cyclic acyl having up to 14 carbon atoms, hydroxyalkyl, straight-chain or branched alkoxycarbonyl or acyloxyalkyl having in each case up to 6 carbon atoms, or a radical of the formula —$SO_2R^{14}$
in which
$R^{14}$ represents straight-chain or branched alkyl having up to 4 carbon atoms,
and/or
$R^{12}$ and $R^{13}$ also represent radicals of the formulae

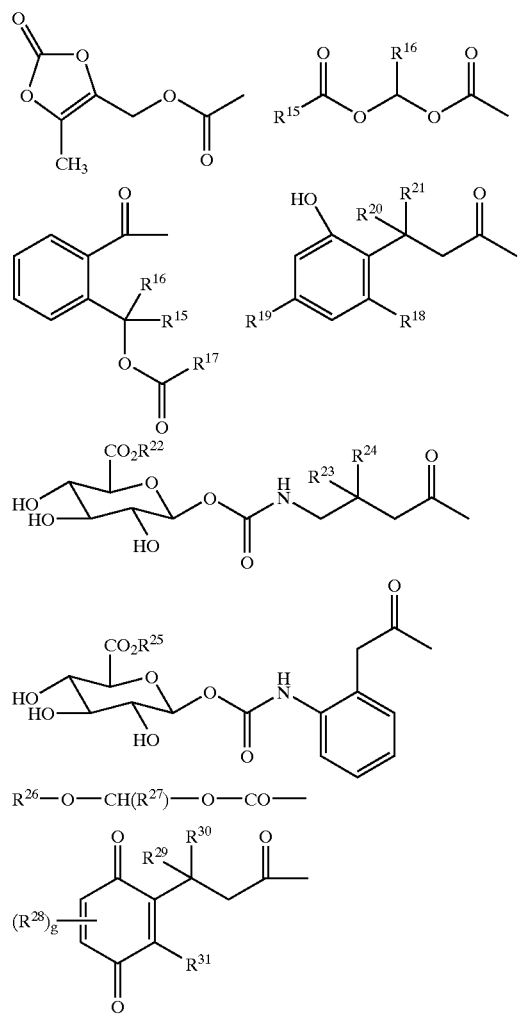

in which
$R^{15}$–$R^{16}$ and $R^{18}$–$R^{31}$ are identical or different and each represents hydrogen or straight-chain or branched alkyl having, up to 4 carbon atoms,
g represents a number 0, 1 or 2,
and
$R^{17}$ represents phenyl, straight-chain or branched alkyl having up to 6 carbon atoms or cycloalkyl having 3 to 8 carbon atoms, with the proviso that, if e=0, $R^{12}$ and $R^{13}$ do not simultaneously represent hydrogen, or $R^1$ represents a purine radical which may optionally be substituted up to three times by halogen, azido, cyano, hydroxyl, amino, monoalkylamino having up to 5 carbon atoms, dialkylamino having in each case up to 5 carbon atoms, alkyl having up to 5 carbon atoms and/or alkoxy having up to 5 carbon atoms, $R^2$ and $R^3$, together with the double bond, form a fused pyridyl, pyrimidinyl, pyrazinyl or pyridazinyl ring, which are optionally substituted up to 2 times by identical or different substituents from the group consisting of formyl, carboxyl, hydroxyl, mercaptyl, straight-chain or branched acyl, alkylthio or alkoxycarbonyl having in each case up to 5 carbon atoms, nitro, cyano, azido, fluorine, chlorine, bromine or straight-chain or branched alkyl or alkoxy having in each case up to 5 carbon atoms which for its part may be substituted by hydroxyl, amino, carboxyl, straight-chain or branched acyl, alkoxy or alkoxycarbonyl having in each case up to 4 carbon atoms, and/or the abovementioned heterocyclic rings are optionally substituted by a group of the formula $-NR^{32}R^{33}$ in which $R^{32}$ and $R^{33}$ are identical or different and represent hydrogen or straight-chain or branched alkyl having up to 4 carbon atoms or $R^{32}$ represents hydrogen and $R^{33}$ represents formyl and/or the abovementioned fused pyridyl, pyrimidinyl, pyrazinyl or pyridazinyl rings are optionally substituted by phenyl which for its part may be substituted by fluorine, chlorine, bromine or by straight-chain or branched alkyl or alkoxy having in each case up to 4 carbon atoms, A represents thienyl, tetrahydropyranyl, tetrahydrofuranyl, phenyl, morpholinyl, pyrimidyl, pyrazinyl, pyridazinyl or pyridyl which are optionally substituted up to 2 times by identical or different substituents from the group consisting of hydroxyl, formyl, carboxyl, straight-chain or branched acyl, alkylthio, alkyloxyacyl, alkoxy or alkoxycarbonyl having in each case up to 4 carbon atoms, fluorine, chlorine and bromine, and their isomeric forms and salts.

Particular preference according to the invention is given to compounds of the general formula (1) according to claim 1 in which $R^1$ represents a pyrimidine radical which is optionally substituted up to 2 times by identical or different radicals from the group (i) consisting of hydrogen, amino, hydroxyl, alkoxy or alkoxycarbonyl having in each case up to 3 carbon atoms, cyano or halogen, and which is substituted by at least one radical from the group (ii) consisting of a 5- to 6-membered ring which may be saturated, unsaturated or partially unsaturated, which contains 1 to 3 heteroatoms from the group consisting of N, O, S, SO, $SO_2$ and which may also be attached via N, imidazolyl, imidazolinyl, imidazolidinyl, morpholinyl, piperidinyl, piperazinyl, pyrrolidinyl, triazolyl, pyrrolyl and thiomorpholinyl being particularly preferred, and which is optionally mono- or polysubstituted by a 5-membered ring which contains two oxygen atoms as ring members and which forms, with the 3- to 8-membered ring, a bicyclic unit or a spiro unit, such as, for example, a 1,4-dioxa-8-azaspiro[4.5]decane or 1,5-dioxa-9-azaspiro[5.5]undecane radical, and/or by hydroxyl, cyano, straight-chain or branched alkyl, acyl or alkoxycarbonyl having in each case up to 3 carbon atoms, where alkyl, acyl and alkoxycarbonyl may be substituted by hydroxyl, amino, halogen, carboxyl, straight-chain or branched acyl or alkoxy having in each case up to 3 carbon atoms, and a tolyl radical, and $C_7$-alkyl which is optionally substituted by cyano, and $(C_1-C_5)$alkyl, which is 1- to 3-times substituted by halogen(s), cyano, aryl and acyloxy, and —NO or radicals of the formula $-S(O)_dR^9$, in which d represents a number 1 or 2, $R^9$ represents straight-chain or branched alkyl having 1 to 4 carbon atoms, aryl having 6 carbon atoms or thienyl, and a radical of the formula $PO(OR^{10})(OR^{11})$, in which $R^{10}$ and $R^{11}$ are identical or different and each represents straight-chain or branched alkyl having up to 3 carbon atoms, and radicals of the formulae $-NH-C(=NH)NH_2$ and $(CO)_eNR^{12}R^{13}$ in which e represents a number 0 or 1, $R^{12}$ and $R^{13}$ are identical or different and each represents hydrogen, straight-chain or branched alkyl having up to 4 carbon atoms or cycloalkyl having 3 carbon atoms, where the abovementioned radicals may optionally be substituted by aryl having 6 carbon atoms, furyl, cycloalkyl having 3 carbon atoms, hydroxyl, straight-chain alkoxy having up to 2 carbon atoms, and, in the case that e=1, $R^{12}$ and $R^{13}$, together with the nitrogen atom to which they are attached, may also form a 5- or 6-membered ring having up to 2 heteroatoms from the group consisting of N, O, S which may optionally be substituted up to 2 times by hydroxyl or methyl, and, in the case that e=0, $R^{12}$ and $R^{13}$ may also represent straight-chain acyl having up to 14 carbon atoms [lacuna] having up to 2 carbon atoms, and/or $R^{12}$ and $R^{13}$ also represent a radical of the formula

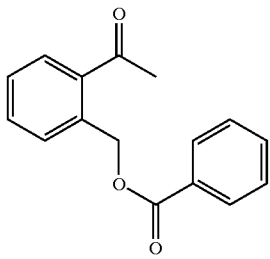

with the proviso that in the case that e=0, $R^{12}$ and $R^{13}$ do not simultaneously represent hydrogen, or $R^1$ represents a purine radical which may optionally be substituted up to two times by halogen, azido, amino, monoalkylamino having up to 4 carbon atoms and/or methyl, $R^2$ and $R^3$, together with the double bond, form a pyridyl or pyrimidinyl ring, A represents phenyl or pyrimidyl, which are optionally substituted by fluorine, chlorine or bromine, and their isomeric forms and salts.

Particular preference according to the invention is given to compounds of the general formula (I) in which $R^1$ represents a radical of the formula

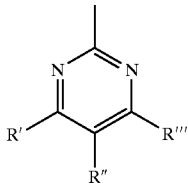

in which

R' represents $NH_2$,

R" represents optionally substituted morpholinyl, piperidinyl, piperazinyl, pyrrolidinyl, triazolyl or thiomorpholinyl and R'" represents hydrogen or $NH_2$.

Very particular preference is given here to compounds in which R" represents morpholinyl.

The compounds of the general formula (I) according to the invention may also be present in the form of their salts. In general, salts with organic or inorganic bases or acids may be mentioned here.

In the context of the present invention, preference is given to physiologically acceptable salts. Physiologically acceptable salts of the compounds according to the invention may be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedispulphonic acid, acetic acid, propionic acid, lactic acid, tartaric acid, citric acid, fumaric acid, maleic acid or benzoic acid.

Physiologically acceptable salts may also be the metal or ammonium salts of the compounds according to the invention which have a free carboxyl group. Particular preference is given, for example, to sodium, potassium, magnesium or calcium salts, and to ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention may exist in stereoisomeric forms which are either like image and mirror image (enantiomers) or which are not like image and mirror image (diastereomers). The invention relates both to the enantiomers or diastereomers and to their respective mixtures. The racemates, like the diastereomers, can be separated into stereoisomerically uniform components in a known manner.

In the context of the present invention, the substituents have, unless indicated otherwise, generally the following meanings:

Alkyl generally represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodecyl, eicosyl.

Alkenyl generally represents a straight-chain or branched hydrocarbon radical having 2 to 20 carbon atoms and one or more, preferably one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.

Alkinyl generally represents a straight-chain or branched hydrocarbon radical having 2 to 20 carbon atoms and one or more, preferably one or two, triple bonds. Examples which may be mentioned are ethinyl, 2-butinyl, 2-pentinyl and 2-hexinyl.

Acyl generally represents straight-chain or branched lower alkyl having 1 to 9 carbon atoms which is attached via a carbonyl group. Examples which may be mentioned are: acetyl, ethylcarbonyl, propylcarbonyl, isopropylcarbonyl, butylcarbonyl and isobutylcarbonyl.

Alkoxy generally represents a straight-chain or branched hydrocarbon radical having 1 to 14 carbon atoms which is attached via an oxygen atom. Examples which may be mentioned are methoxy, ethoxy, propoxy, isopropoxy, butoxy, isobutoxy, pentoxy isopentoxy, hexoxy, isohexoxy, heptoxy, isoheptoxy, octoxy or isooctoxy. The terms "alkoxy" and "alkyloxy" are used synonymously.

Alkoxyalkyl generally represents an alkyl radical having up to 8 carbon atoms which is substituted by an alkoxy radical having up to 8 carbon atoms.

Alkoxycarbonyl can be depicted, for example, by the formula

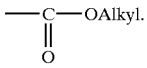

Alkyl here generally represents a straight-chain or branched hydrocarbon radical having 1 to 13 carbon atoms. The following alkoxycarbonyl radicals may be mentioned as examples: methoxycarbonyl, ethoxycarbonyl, propoxycarbonyl, isopropoxycarbonyl, butoxycarbonyl or isobutoxycarbonyl.

Cycloalkyl generally represents a cyclic hydrocarbon radical having 3 to 8 carbon atoms. Preference is given to cyclopropyl, cyclopentyl and cyclohexyl. Examples which may be mentioned are cyclopentyl, cyclohexyl, cycloheptyl and cyclooctyl.

Cycloalkoxy represents, in the context of the invention, an alkoxy radical whose hydrocarbon radical is a cycloalkyl radical. The cycloalkyl radical generally has up to 8 carbon atoms. Examples which may be mentioned are: cyclopropyloxy and cyclohexyloxy. The terms "cycloalkoxy" and "cycloalkyloxy" are used synonymously.

Aryl generally represents an aromatic radical having 6 to 10 carbon atoms. Preferred aryl radicals are phenyl and naphthyl.

Halogen represents, in the context of the invention, fluorine, chlorine, bromine and iodine.

Heterocycle represents, in the context of the invention, a saturated, unsaturated or aromatic 3- to 10-membered, for example 5- or 6-membered, heterocycle which may contain up to 3 heteroatoms from the group consisting of S, N and O and which, in the case of a nitrogen atom, may also be attached via this nitrogen atom. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3-triazolyl, thiazolyl, oxazolyl, imidazolyl, morpholinyl or piperidyl. Preference is given to thiazolyl, furyl, oxazolyl, pyrazolyl, triazolyl, pyridyl, pyrimidinyl, pyridazinyl and tetrahydropyranyl. The term "heteroaryl" (or "hetaryl") represents an aromatic heterocyclic radical.

The invention furthermore provides a process for preparing compounds of the general formula (I) where, depending on the various meanings of the heterocycles listed above under $R^2$ and $R^3$,

[A] compounds of the general formula (II)

$$R^1—D \quad (II),$$

in which
$R^1$ is as defined above
and
D represents radicals of the formulae

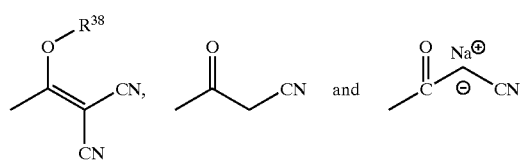

in which
$R^{38}$ represents $C_1$–$C_4$-alkyl are converted, by reaction with compounds of the general formula (III)

$$A—CH_2—NH—NH_2 \quad (III)$$

in which
A is as defined above in inert solvents, if appropriate in the presence of a base, into the compounds of the general formula (IV) or (IVa)

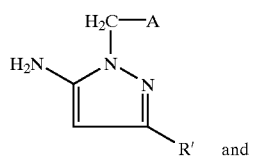

and

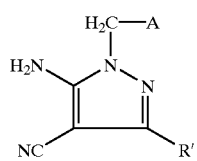

in which
A and $R^1$ are each as defined above, and, in the case of the compounds of the general formula (IVa), are subsequently cyclized with carboxylic acids, nitrites, formamides or guanidium salts, and, in the case of the compounds of the general formula (IV), are cyclized with 1,3-dicarbonyl derivatives, their salts, tautomers, enol ethers or enamines, in the presence of acids and, if appropriate, under microwave irradiation, or

[B] in the case that $R^2$ and $R^3$ together form a pyrazine ring, compounds of the general formula (IV) are initially converted by nitrosation into the compounds of the general formula (V)

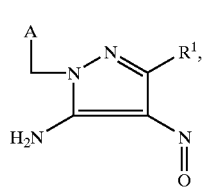

in which
A and $R^1$ are each as defined above, in a second step, the compounds of the general formula (VI)

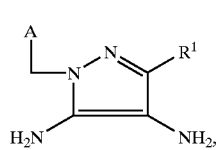

in which
A and $R^1$ are each as defined above are prepared by a reduction, and these are subsequently cyclized with 1,2-dicarbonyl compounds, preferably aqueous glyoxal solution, or

[C] compounds of the general formula (VII)

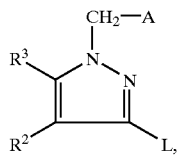
(VII)

in which

A$^1$, R$^2$ and R$^3$ are each as defined above and

L represents a radical of the formula —SnR$^{39}$R$^{40}$R$^{41}$, Zn$^{42}$, iodine, bromine or triflate in which R$^{39}$, R$^{40}$ and R$^{41}$ are identical or different and each represents straight-chain or branched alkyl having up to 4 carbon atoms and R$^{42}$ represents halogen are reacted with compounds of the general formula (VIII)

R$^1$—T   (VIII), in which

R$^1$ is as defined above and in the case that L=SnR$^{39}$R$^{40}$R$^{41}$ or ZnR$^{42}$, T represents triflate or represents halogen, preferably bromine and, in the case that L=iodine, bromine or triflate, T represents a radical of the formula SR$^{39'}$R$^{40'}$R$^{41'}$, ZnR$^{42'}$ or BR$^{43'}$R$^{44'}$ in which R$^{39'}$, R$^{40'}$, R$^{41'}$ and R$^{42'}$ have the meanings of R$^{39}$, R$^{40}$, R$^{41}$ and R$^{42}$ given above and are identical to or different from them, R$^{43'}$ and R$^{44'}$ are identical or different and each represents hydroxyl, aryloxy having 6 to 10 carbon atoms or straight-chain or branched alkyl or alkoxy having in each case up to 5 carbon atoms, or together form a 5- or 6-membered carbocyclic ring in a palladium-catalysed reaction in inert solvents, if appropriate in the presence of a base, or

[D] in the case that R$^1$ represents an optionally substituted pyrimidine radical, amidines of the general formula (IX)

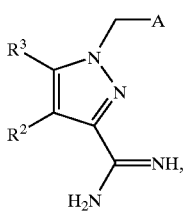
(IX)

in which

A, R$^2$ and R$^3$ are each as defined above are reacted, for example, with compounds of the general formula (X), (Xa), (Xb) or (Xc)

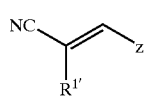
(X)

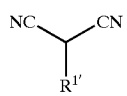
(Xa)

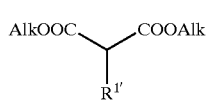
(Xb)

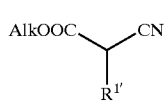
(Xc)

in which

R$^{1'}$ represents the optionally substituted cycloalkyl radical listed above under R$^1$;

Alk represents straight-chain or branched alkyl having up to 8 carbon atoms, preferably up to 4 carbon atoms;

and

Z represents an NH$_2$ group, a monoalkylamino group having up to 7 carbon atoms, a dialkylamino group having up to 7 carbon atoms, a piperidinyl or morpholinyl radical which is attached via the nitrogen, hydroxyl, alkoxy having up to 7 carbon atoms, acyloxy having up to 7 carbon atoms or aroyloxy having 6 to 10 carbon atoms, and, in the case of the groups —S(O)$_c$NR$^6$R$^7$ and —S(O)$_c$NR$^{6'}$R$^{7'}$, starting from the unsubstituted compounds of the general formula (I), reacted initially with thionyl chloride and, in a second step, with the appropriate amines and, if appropriate, the substituents listed under X, Y, R$^1$, R$^2$, R$^3$ and/or R$^4$ are modified or introduced by customary methods, preferably by acylation of free amino groups or hydroxyl groups, chlorination, catalytic hydrogenation, reduction, oxidation, removal of protective groups and/or nucleophilic substitution.

By way of example, the process according to the invention can be illustrated by the following equations:
Process [A]
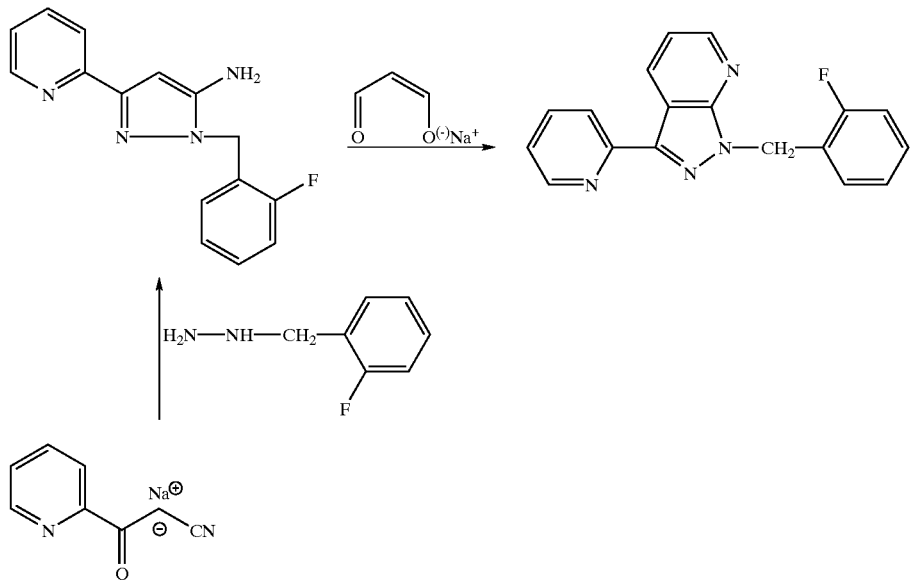
Process [C]
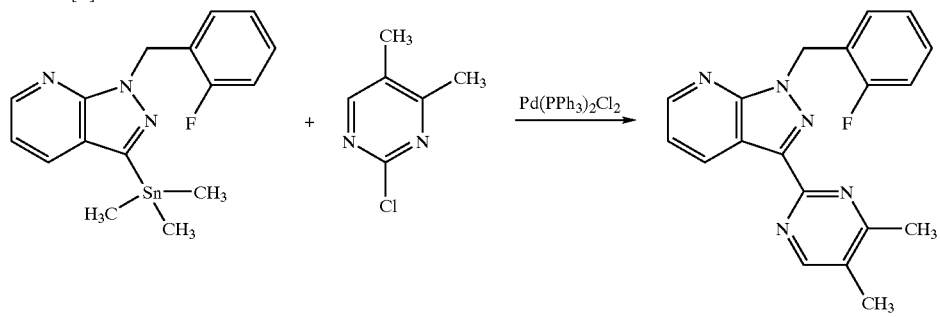
Process [D]
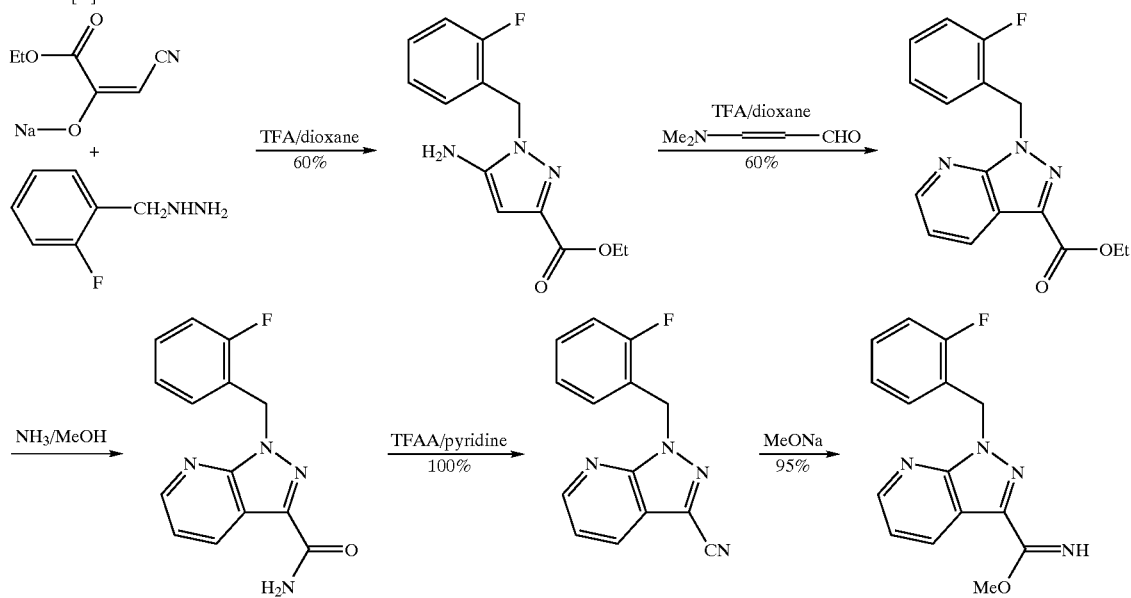

-continued

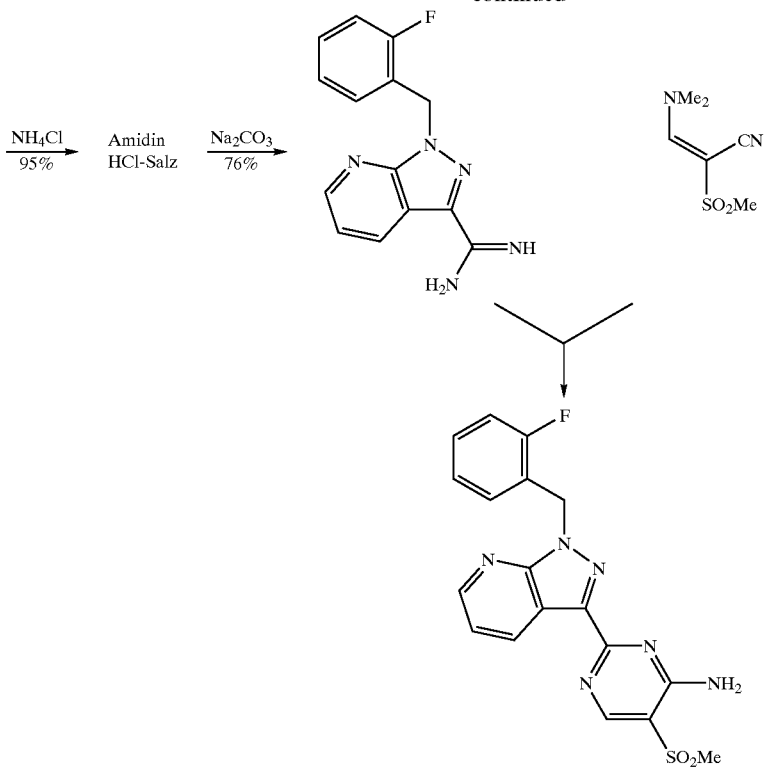

The heterocycles listed under $R^2$ and $R^3$ can also be introduced by reacting the appropriately substituted compounds according to other known heterocyclic syntheses.

Suitable solvents for the individual steps of process [A] and [B] are inert organic solvents which do not change under the reaction conditions. These include ethers, such as diethyl ether or tetrahydrofuran, DME, dioxane, alcohols, such as methanol and ethanol, halogenated hydrocarbons, such as dichloromethane, trichloromethane, carbon tetrachloride, 1,2-dichloroethane, trichloroethane, tetrachloroethane, 1,2-dichloroethane or trichloroethylene, hydrocarbons, such as benzene, xylene, toluene, hexane, cyclohexane, or mineral oil fractions, nitromethane, dimethylformamide, acetone, acetonitrile or hexamethylphosphoric triamide. It is also possible to use mixtures of the solvents. Particular preference is given to tetrahydrofuran, dimethylformamide, toluene, dioxane or dimethoxyethane.

Bases which are suitable for use in the processes according to the invention are, in general, inorganic or organic bases. These preferably include alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alkoxides, such as sodium methoxide or potassium methoxide, sodium ethoxide or potassium ethoxide or potassium tert-butoxide, or organic amines (trialkyl($C_1$–$C_6$)-amines), such as triethylamine, or heterocycles, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to use alkali metals, such as sodium, and their hydrides, such as sodium hydride, as bases. Preference is given to sodium carbonate and potassium carbonate, triethylamine and sodium hydride.

When reacting the compounds of the formula (II) with the compounds of the formula (III), the base is employed in an amount of from 1 mol to 5 mol, preferably from 1 mol to 3 mol, based on 1 mol of the compound of the general formula (II).

The reaction of the compounds of the formula (II) with the compounds of the formula (III) is generally carried out in a temperature range of from 0° C. to 150° C., preferably from +20° C. to +110° C.

This reaction can be carried out at atmospheric pressure or at elevated or reduced pressure (for example from 0.5 to 5 bar). In general, the reaction is carried out at atmospheric pressure.

Suitable acids for the cyclization reactions which may have to be carried out in the processes according to the invention are, in general, protic acids. These preferably include inorganic acids, such as, for example, hydrochloric acid or sulphuric acid, or organic carboxylic acids having 1–6 C atoms which are optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals, such as, for example, methanesulphonic acid, ethanesulphonic acid, benzenesulphonic acid or toluenesulphonic acid.

The catalectic hydrogenation reactions which may have to be carried out in the processes according to the invention can generally be carried out with hydrogen in water or in inert organic solvents, such as alcohols, ethers or halogenated hydrocarbons, or mixtures thereof, using catalysts such as raney nickel, palladium, palladium on animal charcoal or platinum, or using hydrides or boranes in inert solvents, if appropriate in the presence of a catalyst.

The chlorination reactions which may have to be carried out in the processes according to the invention are generally carried out using the customary chlorinating agents, such as, for example, PCl$_3$, PCl$_5$, POCl$_3$ or elemental chlorine. In the context of the invention, preference is given to POCl$_3$.

The acylations of free amino groups or hydroxyl groups which may have to be carried out in the processes according to the invention can be carried out by customary methods which are known to the person skilled in the art. It is possible, for example, to convert appropriate free amino groups or hydroxyl groups by reaction with an acyl halide, preferably an acyl chloride, or an acetic anhydride, in the presence of a base, such as, for example, sodium hydride, pyridine or dimethylaminopyridine in a solvent such as tetrahydrofuran or dichloromethane into the respective amides or esters, or to convert them into the respective sulphonamides or sulphonic esters by reaction with a sulphonyl halide, preferably a sulphonyl chloride.

The oxidations of thioether groups to sulphoxide groups or sulphone groups which may have to be carried out in the processes according to the invention can be carried out by customary methods known to the person skilled in the art. Such oxidations can, for example, be carried out using m-chloroperoxybenzoic acid (MCPBA) in a solvent such as dichloromethane.

The nucleophilic substitutions and Vilsmeier reactions which may have to be carried out in the processes according to the invention are carried out by customary methods known to the person skilled in the art.

The nitrosation of the compounds of the formula (IV) to the compounds of the formula (V), which constitutes the first step of the process [B], can be carried out in accordance with the procedure of P. G. Baraldi et al., Synthesis 1984, 148.

The reductions which may have to be carried out in the processes according to the invention are generally carried out using reducing agents, preferably those which are suitable for reducing carbonyl to hydroxyl compounds. Particularly suitable here is the reduction with metal hydrides or complex metal hydrides in inert solvents, if appropriate in the presence of a trialkylborane. Preference is given to reduction with complex metal hydrides, such as, for example, lithium borohydride, sodium borohydride, potassium borohydride, zinc borohydride, lithium trialkyl borohydride, diisobutylaluminium hydride or lithium aluminium hydride. The reduction is very particularly preferably carried out using diisobutylaluminium hydride and sodium borohydride.

Here, the reducing agent is generally employed in an amount of from 1 mol to 6 mol, preferably from 1 mol to 4 mol, based on 1 mol of the compounds to be reduced.

The reductions which may have to be carried out in the processes according to the invention are generally carried out in a temperature range of from −78° C. to +50° C., preferably from −78° C. to 0° C. in the case of DIBAH and 0° C. to room temperature in the case of NaBH$_4$.

The reductions which may have to be carried out in the processes according to the invention are generally carried out at atmospheric pressure. However, it is also possible to operate under elevated or reduced pressure.

The compounds of the general formulae (II) and (III) are known per se, or they can be prepared by customary methods (cf.: J. Hromatha et al., Monatsh. Chem. 1976, 107, 233).

Some of the compounds of the general formulae (IV), (IVa), (V) and (VI) are known, and they can be prepared as described above.

Suitable solvents for the process [C] are inert organic solvents which do not change under the reaction conditions. These include ethers, such as diethyl ether or tetrahydrofuran, DME, dioxane, halogenated hydrocarbons, such as dichloromethane, trichloromethane, carbon tetrachloride, 1,2-dichloroethane, trichloroethane, tetrachloroethane, 1,2-dichloroethylene or trichloroethylene, hydrocarbons, such as benzene, xylene, toluene, hexane, cyclohexane, or mineral oil fractions, nitromethane, dimethylformamide, acetone, acetonitrile or hexamethylphosphoric triamide. It is also possible to use mixtures of the solvents. Particular preference is given to tetrahydrofuran, dimethylformamide, toluene, dioxane or dimethoxyethane.

The reaction of the compounds of the formula (VII) with the compounds of the formula (VIII) is generally carried out in a temperature range of from 0° C. to 150° C., preferably from +20° C. to +110° C.

This reaction can be carried out at atmospheric pressure or at elevated or reduced pressure (for example from 0.5 to 5 bar). In general, the reaction is carried out at atmospheric pressure.

Suitable palladium compounds in the context of the present invention are, in general, PdCl$_2$(P(C$_6$H$_5$)$_3$)$_2$, palladium-bis-dibenzylideneacetone (Pd(dba)$_2$), [1,1'-bis-(diphenylphosphino)ferrocene]-palladium(II) chloride (Pd (dppf)Cl$_2$) or Pd(P(C$_6$H$_5$)$_3$)$_4$. Preference is given to Pd(P (C$_6$H$_5$)$_3$)$_4$.

The compounds of the general formula (VII) are known per se, or they can be prepared by customary methods (cf., for example K. Kirschke in: Houben-Weyl, Methoden der organischen Chemie, Thieme-Verlag Stuttgart, 4th Ed., volume E8b, part 2, 399–763; in particular with respect to pyrazolopyridines: C. R. Hardy in A. R. Katritzky (Ed.), Adv. Het. Chem. 1984, 36, 343–409; in particular with respect to pyrazolopyrimidines: M. H. Elgnadi et al., Adv. Het. Chem. 1987, 41, 319–376). The preparation of the corresponding halogenopyrozolo[3,4-b]pyrimidines and organotin pyrazolo[3,4-b]pyrimidines of the formula (VII) is described in WO 98/23619 and can also be carried out analogously for the corresponding triflate and organotin compounds of the formula (VII).

The compounds of the general formula (VIII) are known and can be prepared by customary methods (cf., for example, M. G. Hoffmann et al. in: Houben-Weyl, Methoden der organischen Chemic, 4th ed., volume E9b, part 1, pp. 1–249; A. Weissenberger et al., The Chemistry of heterocyclic compounds—pyrimidines, 1962, 16; ibid 1970, 16, suppl. 1, ibid 1985, 16, suppl. 2; ibid 1994, 52).

The process [D] is carried out in a temperature range of from 80° C. to 120° C., preferably at from 100° C. to 110° C., or under reflux.

Suitable solvents are, for example, the reagents of the general formula (X), (Xa), (Xb) or (Xc). However, the reaction can also be carried out in other suitable solvents, such as, for example, toluene, methanol or dichloromethane. Low-boiling solvents, such as, for example, dichloromethane, can be distilled off during the course of the reaction.

The process [D] can be carried out at atmospheric pressure or at elevated or reduced pressure (for example from 0.5 to 5 bar). In general, the process is carried out at atmospheric pressure.

Here, the reaction can either proceed in one step or via open-chain compounds such as, for example,

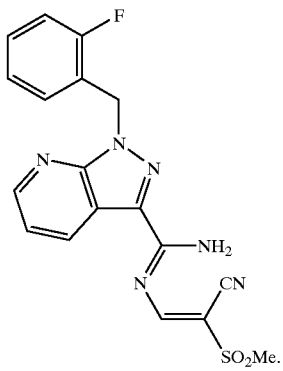

The reaction can be carried out under reduced pressure. It can proceed both with or without addition of the abovementioned solvents, acid or base.

The amidines of the general formula (IX) can be prepared by reacting the compounds of the general formula (XI)

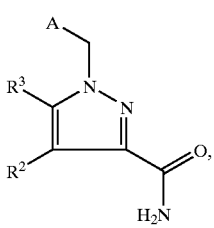

(XI)

in which

A, $R^2$ and $R^3$ are each as defined above initially in ethers with trifluoroacetic anhydride (TFAA) and in the presence of bases to give the compound of the general formula (XII)

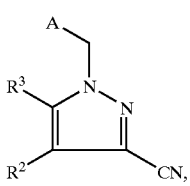

(XII)

in which

A, $R^2$ and $R^3$ are each as defined above, subsequently preparing the compounds of the general formula (XIII)

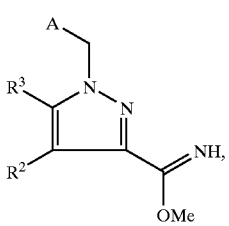

(XIII)

in which

A, $R^2$ and $R^3$ are each as defined above using sodium methoxide, in a next step converting these compounds by reaction with $NH_4Cl$ and glacial acetic acid in alcohols into the corresponding anidine HCl salt of the general formula (XIV)

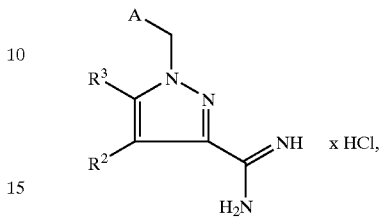

(XIV)

in which

A, $R^2$ and $R^3$ are each as defined above and, in a last step, reacting with bases, preferably sodium carbonate, or alkali metal alkoxide, such as sodium ethoxide.

Suitable solvents for reacting the compounds of the general formula (XI) to give the compounds of the formula (XII) are ethers, such as diethyl ether or tetrahydrofuran, dimethylformamide and dioxane; preference is given to tetrahydrofuran.

Suitable for use as bases here are organic amines (trialkyl ($C_1$–$C_6$)-amines) such as triethylamine, or heterocycles, such as 1,4-diazabicyclo[2.2.2]octane (DABCO), 1,8-diazabicyclo[5.4.0]undec-7-ene (DBU), pyridine, dimethylaminopyridine, methylpiperidine or morpholine. Preference is given to pyridine.

The reaction is carried out in a temperature range of from 0° C. to 40° C., preferably at room temperature.

The reaction can be carried out at atmospheric pressure or at elevated or reduced pressure (for example from 0.5 to 5 bar). In general, the reaction is carried out at atmospheric pressure.

The amide (XI) can be prepared, for example, by hydrolysing an appropriate ester as starting material with a base to give the acid, converting the acid into the acyl chloride by customary methods, for example using $SOCl_2$ or $POCl_3$, followed by reaction with ammonia.

The elimination of water from the amide (XI) to given the nitrile (XII) can be carried out with any customary dehydrating agent. Preference according to the invention is given to trifluoroacetic anhydride (TFAA).

The nitrile of the formula (XII) can be converted into the iminoether of the formula (XIII) both under acidic conditions, such as, for example, with HCl/alcohol mixtures, and under basic conditions, such as, for example, with methanol/sodium methoxide. It is generally carried out at from 0° C. to 40° C., for example at room temperature.

Suitable solvents for converting the compounds of the general formula (XIII) into the compounds of the formula (XIV) are alcohols, such as methanol or ethanol. Preference is given to methanol.

The reaction is carried out in a temperature range of from 0° C. to 40° C., preferably at room temperature.

The reaction can be carried out under atmospheric pressure or under elevated or reduced pressure (for example from 0.5 to 5 bar). In general, the reaction is carried out at atmospheric pressure.

Suitable bases for liberating the compounds of the general formula (IX) from compounds of the general formula (XIV) are inorganic or organic bases. These include, for example, alkali metal hydroxides, such as sodium hydroxide or potassium hydroxide, alkaline earth metal hydroxides, such as barium hydroxide, alkali metal carbonates, such as sodium carbonate or potassium carbonate, alkaline earth metal carbonates, such as calcium carbonate, and alkali metal alkoxides, such as sodium methoxide. Preference is given to sodium carbonate and sodium methoxide.

The pyrimidine ring is prepared by customary methods (cf., for example, M. G. Hoffmann et al. in: Houben-Weyl, Methoden der organischen Chemie, 4th ed., volume E9b, part 1, pp. 1–249; A. Weissenberger et al., The Chemistry of heterocyclic compounds—pyrimidines, 1962, 16; ibid 1970, 16, suppl. 1, ibid 1985, 16, suppl. 2; ibid 1994, 52).

Here, the iminoethers of the formula (XIII) can be used as starting materials and be reacted, for example, with a suitable enamine. However, it is also possible to convert the iminoether first, using ammonia or its salts, into a corresponding amidine and to react this either as the free base (IX) or as a salt (XIV) with enamines, acetals, enol ethers, aldehydes, enolates, malononitrile esters or malonodinitriles.

The enamines which may have to be used in this reaction can be prepared, for example, from C—H-acidic compounds, such as acetonitrile derivatives, according to known methods, by reaction with dimethylformamide derivatives, such as, for example, bis(dimethylamino)-tert-butoxymethane, dialkoxy-dialkylamino-methanes.

The compounds of the general formula (XI) can be prepared by converting the compounds of the general formula (XV)

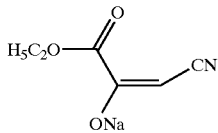
(XV)

with the compounds of the general formula (XVI)

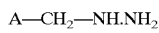
A—CH$_2$—NH.NH$_2$ (XVI)

in ethers, preferably dioxane, and trifluoroacetic acid into the compounds of the general formula (XVII)

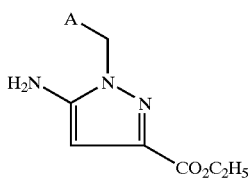
(XVII)

subsequently preparing, by reaction with the compounds of the general formula (XVIII)

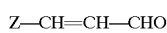
Z—CH=CH—CHO (XVIII)

in which

Z is as defined above, in particular —N(CH$_3$)$_2$ in inert solvents, preferably dioxane, the compounds of the general formula (XIX)

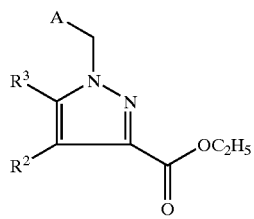
(XIX), followed in a last step by treatment with ammonia in methanol.

Instead of the sodium salt of the enolate (XV), it is also possible to employ enol ethers, ketones or enamines.

If appropriate, the reaction of the compounds of the general formulae (XV) and (XVI) to give (XVII) can also be carried out via intermediates of the formulae (A) and (B),

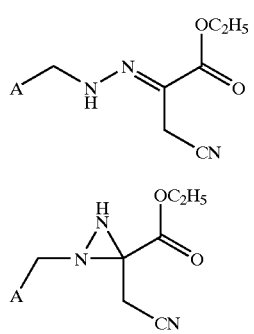

at room temperature.

The compounds of the general formula (X) can be prepared, for example, by reacting the compounds of the formula (XX) or (XXa)

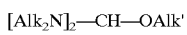
[Alk$_2$N]$_2$—CH—OAlk' (XX)

Alk$_2$N—CH—[OAlk']$_2$ (XXa)

in which

Alk and Alk' are identical or different and each represent straight-chain or branched alkyl having up to 5 carbon atoms with compounds of the formula (XXI)

R$^{1'}$—CH$_2$—CN (XXI)

in which

R$^{1'}$ represents the cycloalkyl radical listed above under R$^1$.

The compounds of the general formulae (XX), (XXa) and (XXI) are known, or they can be prepared by customary methods.

Some of the compounds of the general formulae (XII), (XIII), (XIV), (XV), (XVII), (XVIII) and (XIX) are novel, and they can be prepared as described above.

The pyrimidine radical can also be synthesized with the aid of the reagent of the formula (Xa) which is accessible, for example, as follows:

Compounds of the general formula

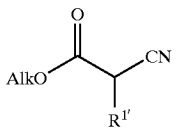
(XXII), in which
R$^{1'}$ is as defined above and Alk represents an alkyl radical having up to 4 carbon atoms
are converted, by using ammonia in suitable solvents, preferably alcohols such as methanol, at temperatures from 0° C. to 40° C., preferably at room temperature, into compounds of the general formula (XIII)

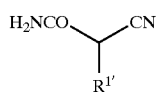
(XXIII), in which R$^{1'}$ is as defined above, and these are subsequently reacted by customary methods with dehydrating agents, such as, for example, Burgess reagent, POCl$_3$, P$_2$O$_5$, SOCl$_2$, trifluoroacetic anhydride/pyridine.

If Burgess reagent is used, the reaction is preferably carried out in inert solvents, such as ethers or chlorinated hydrocarbons. Examples which may be mentioned are dichloromethane and tetrahydrofuran. Preference is given to using a 1:2 mixture of the abovementioned solvents. The reaction is carried out at temperatures from 0° C. to 40° C., preferably at room temperature.

The compounds of the formula (XXII) are known and/or obtainable in a simple manner known to the person skilled in the art.

Some of the compounds of the formula (X) undergo keto-enol tautomerism, for example:

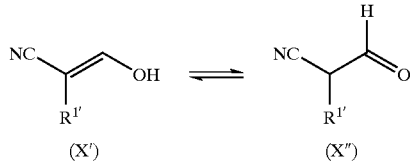

The pyrimidine radical can also be synthesized with the aid of the reagent of the formula (Xa) which is obtainable, for example, as follows:
Compounds of the general formula (XXIIa)

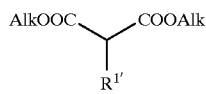
(XXIIa)

in which
R$^1$ is as defined above and
Alk represents an alkyl radical having up to 4 carbon atoms
are converted, using ammonia in suitable solvents, preferably alcohols such as methanol, at temperatures from 0° C. to 40° C., preferably room temperature, into compounds of the general formula (XXIIIa)

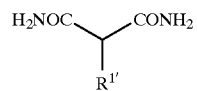
(XXIIIa)

in which R$^{1'}$ is as defined above,
and these are subsequently reacted by customary methods with dehydrating agents, such as, for example, Burgess reagent, POCl$_3$, P$_2$O$_5$, SOCl$_2$, trifluoroacetic anhydride/pyridine.

If Burgess reagent is used, the reaction is preferably carried out in inert solvents, such as ethers or chlorinated hydrocarbons. Examples which may be mentioned are dichloromethane and tetrahydrofuran. Preference is given to using a 1:2 mixture of the abovementioned solvents. The reaction is carried out at temperatures from 0° C. to 40° C., preferably at room temperature.

The compounds of the formula (XXIIa) are known and/or obtainable in a simple manner known to the person skilled in the art.

If typical protective groups are employed in the course of derivatization reaction, their removal is generally carried out in one of the abovementioned alcohols and/or THF or acetone, preferably methanol/THF in the presence of hydrochloric acid or trifluoroacetic acid or toluenesulphonic acid, in a temperature range of from 0° C. to 70° C., preferably at room temperature under atmospheric pressure.

The compounds of the general formula (I) according to the invention have an unforeseeable, valuable spectrum of pharmacological action.

The compounds of the general formula (I) according to the invention lead to a vasorelaxation, inhibition of platelet aggregation and to a fall in blood pressure and also to an increase in coronary blood flow. These actions are mediated via a direct stimulation of soluble guanylate cyclase and an intracellular cGMP increase. Additionally, the compounds of the general formula (I) according to the invention enhance the action of substances which raise the cGMP level, such as, for example, EDRF (endothelium-derived relaxing factor), NO donors, protoporphyrin IX, arachidonic acid or phenylhydrazine derivatives.

They can therefore be employed in medicaments for the treatment of cardiovascular disorders, such as, for example, for the treatment of high blood pressure and cardiac insufficiency, stable and unstable angina pectoris, peripheral and cardiac vascular disorders, arrhythmias, for the treatment of thromboembolic disorders and ischaemias such as myocardial infarct, stroke, transitory and ischaemic attacks, peripheral circulatory disorders, prevention of restenoses such as after thrombolysis therapy, percutaneous translumino angioplastie (PTA), percutaneous transluminalo coronary angioplasty (PTCA), bypass and also for the treatment of arterioscleroses, asthmatic disorders and disorders of the urogenital system such as, for example, prostate hypertrophy, erectile dysfunction, female sexual dysfunction and incontinence.

The compounds of the general formula (I) described in the present invention are also active compounds for controlling disorders in the central nervous system which are characterized by disturbances of the NO/cGMP system. In particular, they are suitable for eliminating cognitive deficits, for improving learning and memory performance and for treating Alzheimer's disease. They are also suitable for the treatment of disorders of the central nervous system such as states of anxiety, tension and depression, sleeping disorders and sexual dysfunction caused by the central nervous system, and for regulating pathological eating disorders or disorders associated with the use of stimulants and drugs.

Furthermore, the active compounds are also suitable for regulating cerebral circulation, and they are therefore effective agents for controlling migraines.

They are also suitable for the prophylaxis and control of the sequelae of cerebral infarcts (Apoplexia cerebri) such as stroke, cerebral ischaemia and skull-brain trauma. The compounds of the general formula (I) according to the invention can also be employed for controlling pain.

Additionally, the compounds according to the invention have antiinflammatory action and can therefore be employed as antiinflammatories.

The invention moreover includes the combination of the compounds of the general formula (I) according to the invention with organic nitrates and NO donors.

Organic nitrates and NO donors in the context of the invention are, in general, substances which display their therapeutic action by the release of NO or NO species. Sodium nitroprusside, glycerol trinitrate, isosorbide dinitrate, isosorbide mononitrate, molsidomine and SIN-1 are preferred.

The invention additionally includes the combination with compounds which inhibit the degradation of cyclic guanosine monophosphate (cGMP). These are, in particular, inhibitors of phosphodiesterases 1, 2 and 5; nomenclature according to Beavo and Reifsnyder (1990) TiPS 11 p. 150 to 155. The action of the compound according to the invention is potentiated and the desired pharmacological effect is increased by these inhibitors.

To determine the cardiovascular action, the following investigations were carried out: In in vitro investigations on the isolated and on cells of vascular origin, the effect on guanylate cyclase-dependent cGMP formation was tested with and without NO donor. The anti-aggregatory properties were shown on human platelets stimulated with collagen. The vasorelaxant action was determined in rabbit aortal rings preconcentrated with phenylephrine. The hypotensive action was investigated in anaesthetized and awake rats.

Stimulation of Recombinant Soluble Guanylate Cyclase in vitro

The investigations on the stimulation of recombinant soluble guanylate cyclase by the compounds according to the invention with and without NO donor were carried out using the method which is described in detail in the following literature reference: M. Hoenicka, E. M. Becker, H. Apeler, T. Sirichoke, H. Schroeder, R. Gerzer and J.-P. Stasch: Purified soluble guanylate cyclase expressed in a baculovirus/Sf9 system: stimulation by YC-1, nitric oxide, and carbon oxide. J. Mol. Med. 77: 14–23 (1999). The results are shown in FIG. 1.

Stimulation of Soluble Guanylate Cyclase in Primary Endothelial Cells

Primary endothelial cells were isolated from pig aortas by treatment with collagenase soln. The cells were then cultured in culture medium at 37□C/5% $CO_2$ until confluence was reached. For the investigations, the cells were passaged, inoculated into 24-well cell culture plates and subcultured until reaching confluence (~$2\times10^5$ cells/well). For the stimulation of endothelial guanylate cyclase, the culture medium was aspirated and the cells were washed once with Ringer solution. After removing the Ringer solution, the cells were incubated for 10 minutes at 37° C./5% $CO_2$ in stimulation buffer with or without NO donor (sodium nitroprusside, SNP or DEA/NO 1 $\mu$M). Following this, the test substances (final concentration 1 $\mu$M) were added to the cells by pipette, and they were incubated for a further 10 minutes. After the incubation time had ended, the buffer solution was aspirated and cold buffer at 4° C. was added to the cells. The cells were then lysed at −20° C. for 16 hours. The supernatants containing the intracellular cGMP were then removed and the cGMP concentration was determined by means of the cGMP-SPA system (Amersham Buchler, Brunswick). The results are shown in Tables 1 and 2 below:

TABLE 1

Stimulation of soluble guanylate cyclase in primary endothelial cells

| Example No. | Increase in the cGMP concentration (%) |
| --- | --- |
| 1 | >1000 |
| 2 | >1000 |
| 3 | >1000 |
| 6 | 600 |
| 13 | >1000 |
| 14 | >1000 |

TABLE 2

Stimulation of soluble guanylate cyclase in primary endothelial cells by 3-(4,6-diamino-5-N-morpholinopyrimidin-2-yl)-1-(2-fluorobenzyl)-1H-pyrazolo[3,4-b]-pyridine (Ex. 16)

| Ex. 16 ($\mu$M) | cGMP (pmol/well) |
| --- | --- |
| 0 | 1.7 |
| 0.1 | 5.1 |
| 0.3 | 13.2 |
| 1.0 | 20.8 |
| 3.0 | 34.5 |
| 10 | 47.7 |

Vasorelaxant Action in vitro

Rabbits are anaesthetized by a blow to the neck and exanguinated. The aorta is removed, freed from adhering tissue, divided into 1.5 mm wide rings and individually transferred under a pretension into 5 ml organ baths containing a warm, carbogen-aerated Krebs-Henseleit solution at 37° C. of the following composition (mM): NaCl: 119; KCl: 4.8; $CaCl_2\times2H_2O$: 1; $MgSO_4\times7H_2O$: 1.4; $KH_2PO_4$: 1.2; $NaHCO_3$: 25; glucose: 10. The contractility is detected using Statham UC2 cells, amplified and digitalized by means of A/D converters (DAS-1802 HC, Keithley Instruments Munich), and recorded in parallel on linear recorders. To produce a contraction, phenylephrin is added to the bath cumulatively in increasing concentration. After several control cycles, the substance to be investigated is investigated in each further passage in increasing dosage in each case, and the height of the contraction is compared with the height of the contraction achieved in the last preliminary passage. From this, the concentration which is necessary in order to reduce the height of the control value by 50% ($IC_{50}$) is calculated. The standard administration volume is 5 $\mu$l, and the proportion of DMSO in the bath solution corresponds to 0.1%. The results are shown in Table 3 below:

TABLE 3

Vasorelaxant action in vitro

| Example No. | IC$_{50}$ [μM] |
| --- | --- |
| 1 | 0.23 |
| 3 | 0.38 |
| 3 | 0.4 |
| 5 | 0.24 |
| 7 | 3.4 |
| 13 | 0.41 |
| 16 | 0.2 |
| 21 | 0.67 |
| 22 | 0.68 |
| 23 | 0.54 |
| 24 | 0.35 |
| 25 | 0.79 |
| 26 | 1 |
| 27 | 0.18 |
| 28 | 0.22 |
| 31 | 0.53 |
| 32 | 0.58 |
| 33 | 0.62 |
| 35 | 1.8 |
| 71 | 0.7 |
| 73 | 0.69 |
| 77 | 0.76 |
| 78 | 9.5 |
| 79 | 4.1 |

Blood Pressure Measurements in Anaesthetized Rats

Male Wister rats having a bodyweight of 300–350 g are anaesthetized with Thiopental (100 mg/kg i.p.). After tracheotomy, a catheter is inserted into the femoral artery for blood pressure measurement. The substances to be tested are administered orally in Transcutol, Cremophor EL, H$_2$O (10%/20%/70%) in a volume of 1 ml/kg. The results are listed in Table 4 below.

TABLE 4

| Ex. No. | Dose (mg/kg p.o.) | max. reduction in blood pressure (mm Hg) |
| --- | --- | --- |
| 16 | 0.3 | 21 |
| 16 | 1.0 | 35 |

Effect on the Average Blood Pressure of Awake, Spontaneously Hypertensive Rats

Continuous measurements of blood pressure over 24 hours were carried out on spontaneously hypertensive female rats (MOL:SPRD) having a bodyweight of 200–250 g which were allowed to move around freely. To this end, pressure monitors (Data Sciences Inc., St. Paul, Minn., USA) were chronically implanted into the descending abdominal aorta of the animals, below the kidney artery, and the attached transmitter was fixed in the abdominal cavity.

The animals were kept individually in type III cages, which were positioned on the individual receiver stations, and adapted to a 12-hour day/night rhythm. Water and feed was available freely.

To collect the data, the blood pressure of each rat was registered every 5 minutes for 10 seconds. In each case, the data for a period of 15 minutes were collected and the average value was calculated from these values.

Figure 2:
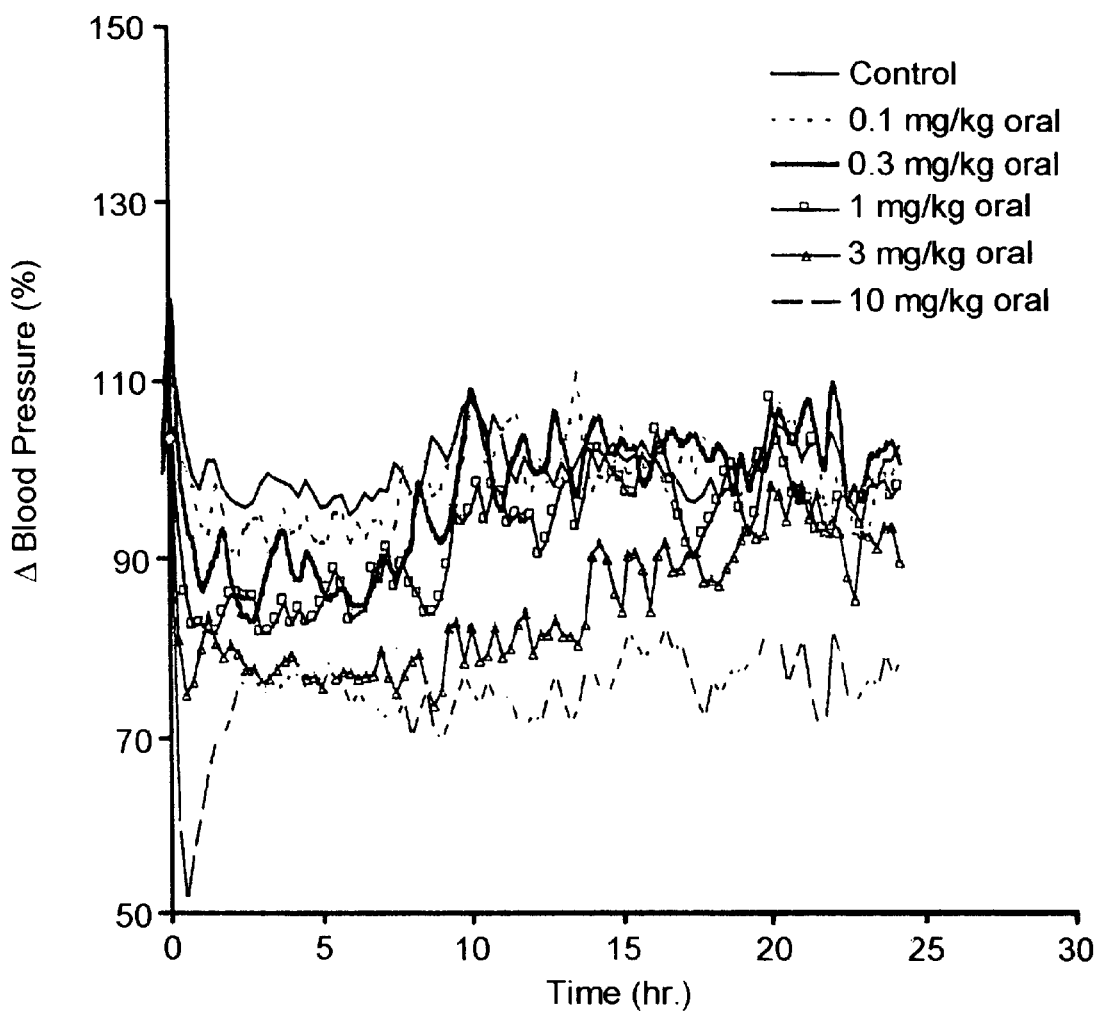
FIG. 2 shows the effect of 3-(4,6-diamino-5-N-morpholino-2-pyrimidinyl)-1-(2-fluorobenzyl)-1H-pyrazolo[3,4-b]pyridine (example 16) on the mean blood pressure of conscious, spontaneously hypertensive rats.

The compounds to be tested were dissolved in a mixture of Transcutol (10%), Cremophor (20%), H$_2$O (70%) and administered orally by means of a stomach tube in a volume of 2 ml/kg of bodyweight. The doses tested were between 0.3 and 30 mg/kg of bodyweight. The results are shown in FIG. 2 (attached).

Inhibition of Platelet Aggregation in vitro

To determine the platelet-aggregation, blood from healthy volunteers of both sexes was used. As an anticoagulant, 9 parts of blood were admixed to one part of 3.8% strength sodium citrate solution. The blood was centrifuged at 900 rpm for 20 min. The pH of the platelet-rich plasma obtained was adjusted to pH 6.5 using ACD solution (sodium citrate/citric acid/glucose). The platelets were subsequently centrifuged off and resuspended in buffer and once more centrifuged off. The platelet pellet was suspended in buffer and mixed with an additional 2 mmol/l of CaCl$_2$.

To measure the aggregation, aliquots of the platelet suspension were incubated with the substance to be tested at 37° C. for 10 min. Aggregation was subsequently induced in an aggregometer by addition of collagen and determined at 37° C. using the turbidometric method according to Born (Born, G. V. R., J. Physiol. (London), 168, 178–195, 1963). The results are shown in Table 5 below.

TABLE 5

| Ex. No. | IC$_{50}$ (μM) |
| --- | --- |
| 16 | 0.06 |

Measurement of the Erection-promoting Action of Guanylate Cyclase Stimulators

For a complete and lasting erection to occur, the cavernous arteries and the entire cavernous body architecture, which is formed by a network of smooth muscle cells and collagen connective tissue, has to be at maximum dilation so that the corpus cavernosum can fill completely with blood (Anderson K.-E. and Wagner G., "Physiology of Penile Erection." Physiological Reviews 75, 191–236 (1995); Meinhardt W. Kropmann R F, Vermeig P, Lycclama a Nigelholt and Zwartendijk J. "The Influence of Medication on Erectile dysfunction." Int. J. of Impotence Res. 9, 17–26 (1997). Relaxation of smooth muscles is mediated by NO which, in the case of sexual stimulation, is released by non-adrenergic, non-cholinergic nerve fibres in the endothelial cells of the blood vessels of the corpus cavernosum. NO activates guanylate cyclase, and the resulting increase in cGMP leads to dilation of the smooth muscles of the corpus cavernosum and consequently to an erection. To test the efficacy of the substances according to the invention, awake rabbits were used. The species rabbit was chosen since neurophysiology, haemodynamic and the control of contraction and relaxation of the smooth muscles of the corpus cavernosum of rabbit and man are quite similar (Meyer M F, Taher H., Krah H., Staubesand J., Becker A J, Kircher M, Mayer B., Jonas U., Forsmann W G., Stief Ch.G. "Intracarvenous Application of SIN-1 in Rabbit and Man: Functional and Toxcological Results." Annals Urol. 27, 179–182 (1993); Taub H C, Lerner S E, Melman A, Christ G J "Relationship between contraction and relaxation in human and rabbit corpus cavernosum." Urology 42, 698–671, (1993).

Method:

Adult male chinchilla rabbits having a weight of 3–5 kg are, after delivery, adapted for several days in isolation. They have free access to water and can feed for two hours per day. The animals are kept in a 10/14 hour day/night rhythm (light switched on from 8.00 hours onwards). The room temperature is 22–24° C.

The animals are weighed directly before the start of the experiment. For intravenous administration, the substances according to the invention were dissolved in a mixture of Transcutol (GATTEFOSSE GmbH) diluted with 20% Cremophor (BASF) and water in a ratio of 3/7. Sodium nitroprusside was dissolved in 0.9% NaCl. The substances were injected at the dosages stated in the table in a volume of 0.5 ml/kg into the auricular vein. For oral administration, the test substances were dissolved in a mixture of glycerol:water:polyethylene glycol 6:10:9.69 and administered at the dosages stated in the table in a volume of 1 ml/kg using the stomach tube.

The effect of guanylate cyclase stimulators is increased by NO donors. This was demonstrated by additionally administering sodium nitroprusside.

The sodium nitroprusside was injected into the auricular vein at a dosage of 0.2 mg/kg simultaneously with the substance according to the invention. If the substance according to the invention was administered orally, the sodium nitroprusside was injected into the auricular vein of these animals 30 min after the oral administration. Corresponding controls were carried out using the solvent and using sodium nitroprusside on its own.

At rest, the penis of the rabbit is not visible in the pubic region and is covered completely by the sheath. The erection is assessed by measuring the length of the protruding penis with a calliper square. Measurements are carried out 5, 10, 15, 30, 45, 60, 120 and 180 min. after the administration of the substance. The effect is calculated as the product of the length of the penis which is not covered by fur in [mm] and the time for which the erection persists in [min].

Intravenous injection of sodium nitroprusside causes an erection which lasts for approximately 10 min. (110 [mm× min.]).

The present invention includes pharmaceutical preparations which, in addition to non-toxic, inert pharmaceutically acceptable excipients, contain the compounds of the general formula (I) according to the invention, and also processes for the production of these preparations.

The active compounds can optionally be present in one or more of the excipients indicated above and also in microencapsulated form.

The therapeutically active compounds of the general formula (I) should be present in the abovementioned pharmaceutical preparations in a concentration from approximately 0.1 to 99.5, preferably from approximately 0.5 to 95, % by weight of the total mixture.

In addition to the compounds of the general formula (I) according to the invention, the abovementioned pharmaceutical preparations can also contain other pharmaceutically active compounds.

In general, it has proved advantageous both in human and in veterinary medicine to administer the active compound(s) according to the invention in total amounts from approximately 0.5 to approximately 500, preferably 5 to 100, mg/kg of bodyweight every 24 hours, if appropriate in the form of several individual doses, to achieve the desired results. An individual dose contains the active compound(s) according to the invention preferably in amounts from approximately 1 to approximately 80, in particular 3 to 30, mg/kg of bodyweight.

Below, the present invention is illustrated in more detail using non-limiting, preferred examples. Unless indicated otherwise, all amounts given refer to per cent by weight.

EXAMPLES

Abbreviations

| RT: | Room temperature |
| --- | --- |
| EA: | Ethyl acetate |
| MCPBA: | m-Chloroperoxybenzoic acid |
| BABA: | n-Butyl acetate/n-butanol/glacial acetic acid/phosphate buffer pH 6 (50:9:25.15; org. phase) |

Mobile Phases for Thin-layer Chromatography

| T1 E1: | toluene/ethyl acetate (1:1) |
| --- | --- |
| T1 EtOH1: | toluene-methanol (1:1) |
| C1 E1: | cyclohexane/ethyl acetate (1:1) |
| C1 E2: | cyclohexane/ethyl acetate (1:2) |

Starting Materials

General Procedure for Preparing 2-Substituted 3-Dimethylaminoacrylonitriles

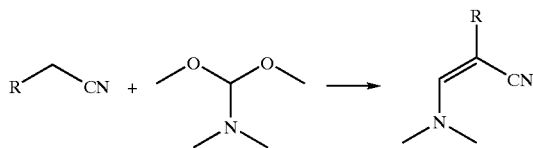

With water-cooling, 50.0 mmol of 2-substituted acetonitrile derivative are added to a solution of 5.95 g (50.0 mmol) of N,N-dimethylformamide dimethyl acetal in 25 ml of abs. methanol, and the mixture is stirred at room temperature for 1 h.

Sulphones: The precipitate is filtered off with suction and dried under high vacuum Phosphonic esters: The solution is freed of methanol initially at 40° C. under 20 mbar using a rotary evaporator, then at room temperature under high vacuum.

| Ex. No. | Starting material | Product | Yield | M.p./NMR |
|---|---|---|---|---|
| 1A | | | 88% | 128° C. |
| 2A | | | 99% | liquid 1H-NMR (400MHz, CDCl$_3$), δ = 1.34(t, 6H, CH$_3$), 3.12(s, 3H, NCH$_3$), 3.31(s, 3H, NCH$_3$), 4.07(m, 4H, CH$_2$), 7.20(d, 1H, olefin-CH). |

Example 3A 3-(Dimethylamino)-2-N-morpholinoacrylonitrile

At 80° C., 8.13 g (64.5 mmol) of morpholinoacetonitrile and 13.3 ml (64.5 mmol) of tert-butoxy-bis(dimethylamino)methane were stirred overnight. The mixture was cooled to room temperature, concentrated using a rotary evaporator and subsequently distilled under reduced pressure.

Yield: 11.0 g (94%) (cis and transisomer). Boiling point: 119° C./0.608 mbar.

Example 4A 3-(Dimethylamino)-2-N-thiomorpholinoacrylonitrile

At 80° C., 6.65 g (46.8 mmol) of N-thiomorpholinoacetonitrile (Wise, L. D. et al., J. Med. Chem., 17, 1974, 1232–1234) and 9.70 ml (47.0 mmol) of tert-butoxy-bis(dimethylamino)methane were stirred overnight. The mixture was cooled to room temperature, concentrated using a rotary evaporator and subsequently distilled under reduced pressure.

Yield: 9.98 g (88% with respect to pure substance, cis and transisomers). Boiling point: 96° C./0.008 mbar.

Example 5A

Ethyl 3-Dimethylamino-2-methylsulphonylacrylate

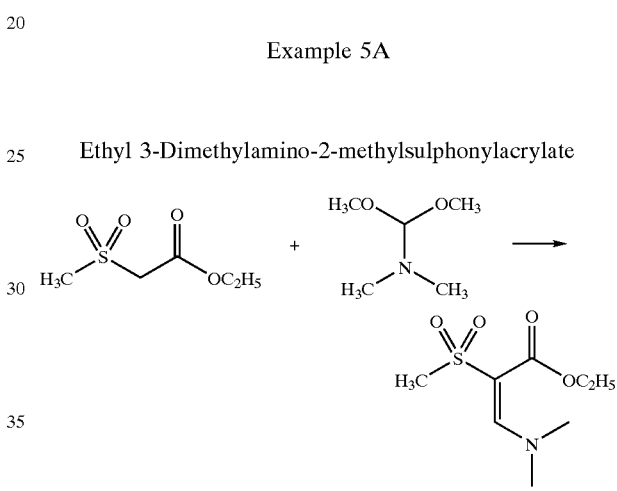

6.65 g (40 mmol) of ethyl methanesulphonylacetate and 5.72 g (48 mmol) of N,N-dimethylformamide dimethyl acetal are admixed and heated at 85° C. overnight. The solution is concentrated using a rotary evaporator, and the solid is comminuted with cyclohexane and filtered off with suction.

Yield: 8.36 g (94.5% of theory).

Example 6A 2-(4-Methylpiperazino)malonodiamide

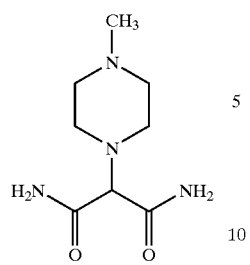

1.00 g (5.52 mmol) of 2-bromomalonodiamide (preparation analogous to Backes, West and Whiteley, J. Chem. Soc. 1921, 119, 359), 0.61 g (6.10 mmol) of N-methylpiperazine and 1.15 g (8.29 mmol) of potassium carbonate are admixed in 10 ml of acetonitrile, and the mixture is heated at 50° C. overnight. The mixture is filtered off and the solid is digested with boiling ethanol and filtered off with suction. The filtrate is concentrated using a rotary evaporator, and the crude product is reacted further.

Yield: 1.14 g (crude yield). Rf (SiO$_2$, BABA): 0.06.

Example 7A 2-(4-Acetylpiperazino)malonodiamide

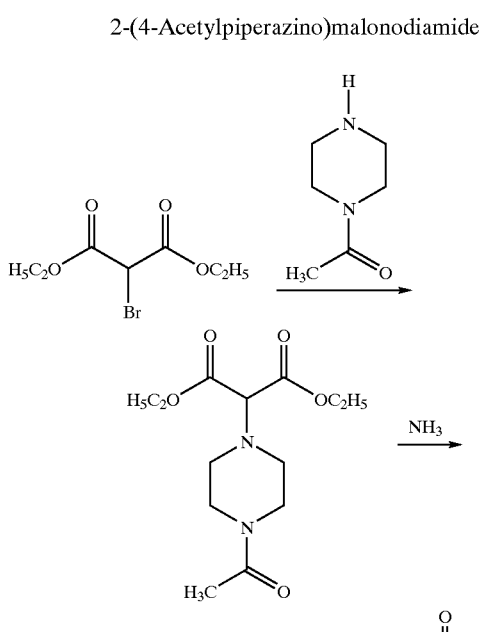

6.16 g (25.8 mmol) of diethyl 2-bromomalonate, 3.63 g (28.3 mmol) of N-acetylpiperazine and 5.34 g (38.6 mmol) of potassium carbonate are admixed in 100 ml of acetonitrile, and the mixture is heated at 50° C. for 28 hours. The reaction mixture is cooled, taken up in 50 ml of ethyl acetate and washed with water. The organic phase is dried over magnesium sulphate and concentrated using a rotary evaporator. Yield: 8.75 g. 7 g of the crude product are dissolved in 70 ml of a solution of ammonia and methanol, and the mixture is stirred at room temperature for 90 hours. The solid is filtered off with suction, washed with cold methanol and dried.

Yield: 2.76 g (49.6% of theory).

Example 8A 2-(4-Methylpiperazine)malonodinitrile

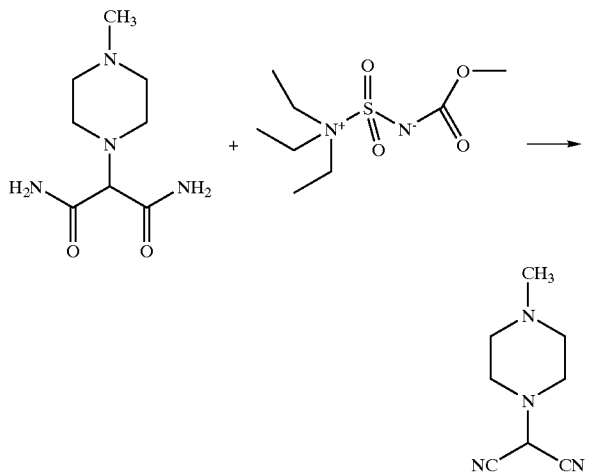

441 mg (2.04 mmol) of 2-(4-methylpiperazine) malonodiamide from Example 6A are dissolved in 20 ml of tetrahydrofuran:dichloromethane (3:1). A total of 1.70 g (7.15 mmol) of Burgess reagent are added in three identical portions at intervals of 30 minutes. After another 30 minutes, the reaction mixture is chromatographed directly over silica gel using ethyl acetate as mobile phase.

Yield: 233 mg (69.4% of theory). Rf (SiO$_2$, EA): 0.22.

Analogously to Examples 6A to 8A, the following compounds were prepared:

| Ex. No. | R | Yield (% of theory) starting from malonodiamide | Rf (SiO$_2$) |
|---|---|---|---|
| 9A | piperidinyl | 80.2 | 0.71 (EA) |
| 10A | N(CH$_3$)CH$_2$CH$_2$OCH$_3$ | 38.1 | 0.66 (EA) |

-continued

| Ex. No. | R | Yield (% of theory) starting from malonodiamide | Rf (SiO$_2$) |
|---|---|---|---|
| 11A | *N-methyl phenylacetamide group* | 36.5 | 0.69 (EA) |
| 12A | *4-methyl-thiomorpholinyl* | 81.6 | 0.74 (EA) |
| 13A | *4-methyl-2,6-dimethylmorpholinyl* | 73.9 | 0.69 (EA) |
| 14A | *4-acetyl-piperazinyl* | 42.9 | 0.32 (EA) |
| 15A | *N-methyl-1,4-dioxa-8-azaspiro[4.5]decyl* | 35.2 | 0.65 (EA) |
| 16A | *4-(2-methoxyethyl)-piperazinyl, N-methyl* | 52.5 | 0.32 (EA) |
| 17A | *1-methyl-4-(ethoxycarbonyl)-piperidinyl* | 47.6 | 0.70 (EA) |
| 18A | *1-methyl-4-cyano-piperidinyl* | 13.4 | 0.68 (EA) |

The preparation of 2-N-morpholinomalonodinitrile, 2-(N,N-dimethylamino)malonodinitrile and 2-(N,N-diethylamino)malonodinitrile is carried out according to H. Gold and O. Bayer, *Chem. Ber.* 1961, 94, 2594.

2-(1,3-thiazol-2-yl)-malononitrile is prepared according to Yamanaka, H.; Ohba, S.; Sakamoto, T. *Heterocycles*, 1990, 31, 1115.

Example 19A 2-(5-Methyl-1,3,4-thiadiazol-2-yl)-malononitrile

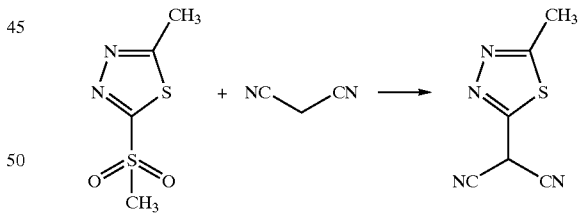

Under argon, 400 mg (10.0 mmol) of sodium hydride (60% suspension in oil) are suspended at room temperature in 40 ml of THF. A solution of 661 mg (10.0 mmol) of malonodinitrile in 10 ml of THF is added dropwise, and the reaction mixture is stirred for 15 min. A solution of 891 mg (5.0 mmol) of 2-methyl-5-methylsulphonyl-1,3,4-thiadiazole in 10 ml of THF is added dropwise. The reaction mixture is heated to 50° C. and stirred overnight, cooled and concentrated using a rotary evaporator. The residue is dissolved in water and adjusted to pH=3 using HCl. A brown solid precipitates out, and this solid is filtered off and dried under reduced pressure.

Yield: 714 mg (87.0% of theory). M.p.: 210° C. (decomp.).

Example 20A

Ethyl 5-Amino-1-(2-fluorobenzyl)-1H-pyrazole-3-carboxylate

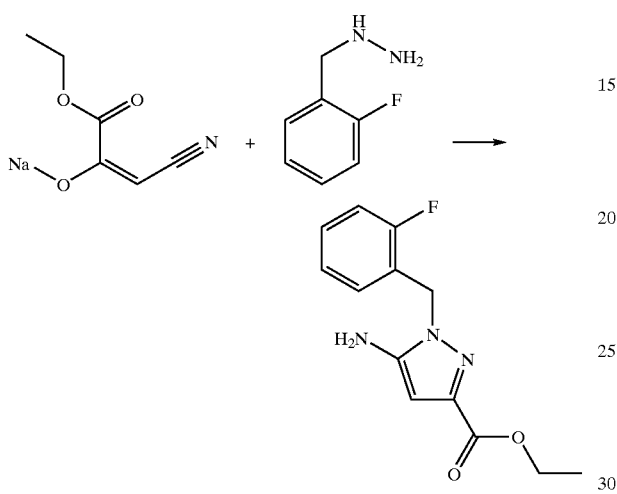

Under argon, 100 g (0.613 mol) of the sodium salt of ethyl cyanopyruvate (preparation analogously to Borsche and Manteuffel, Liebigs Ann. 1934, 512, 97) in 2.5 l of dioxane are admixed, with efficient stirring and at room temperature, with 111.75 g (75 ml, 0.98 mol) of trifluoroacetic acid, and the mixture is stirred for 10 min, during which a large proportion of the starting material dissolves. 85.93 g (0.613 mol) of 2-fluorobenzylhydrazine are then added, and the mixture is boiled overnight. After cooling, the precipitated sodium trifluoroacetate crystals are filtered off with suction and washed with dioxane, and the crude solution is reacted further.

Example 21A

Ethyl 1-(2-Fluorobenzyl)-1H-pyrazolo[3,4-b]pyridine-3-carboxylate

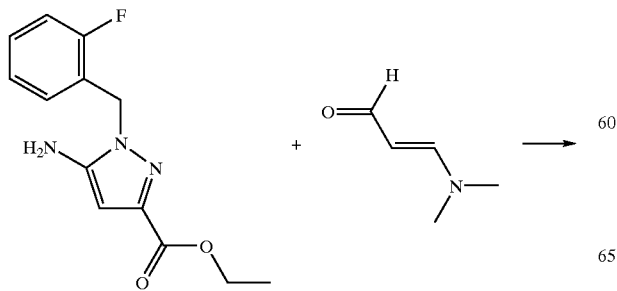

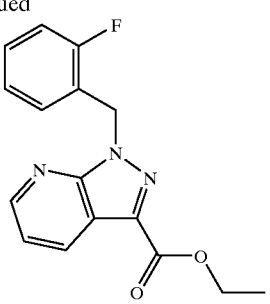

The above solution from Example 20A is admixed with 61.25 ml (60.77 g, 0.613 mol) of dimethylaminoacrolein and 56.28 ml (83.88 g, 0.736 mol) of trifluoroacetic acid, and the mixture is boiled under argon for 3 days. The solvent is subsequently evaporated under reduced pressure and the residue is added to 2 l of water, and the mixture is extracted three times with 1 l of ethyl acetate in each case. The combined organic phases are dried with magnesium sulphate and concentrated using a rotary evaporator. The mixture is chromatographed over 2.5 kg of silica gel and eluted using a toluene/toluene-ethyl acetate=4:1 gradient.

Yield: 91.6 g (49.9% of theory over two steps). M.p. 85° C. Rf (SiO$_2$, T1E1): 0.83.

Example 22A 1-(2-Fluorobenzyl)-1H-pyrazolo[3,4-b]pyridine-3-carboxamide

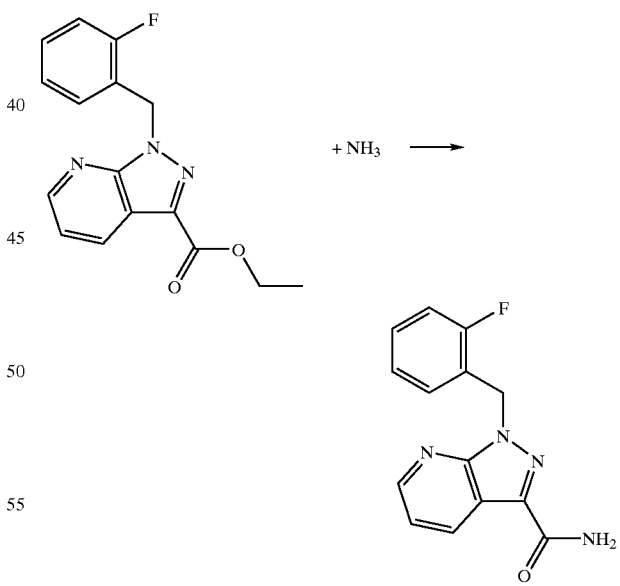

10.18 g (34 mmol) of the ester from Example 21A are initially charged in 150 ml methanol which has been saturated with ammonia at 0–10° C. The mixture is stirred at room temperature for two days and subsequently concentrated under reduced pressure.

Rf (SiO$_2$, T1E1): 0.33.

Example 23A

3-Cyano-1-(2-fluorobenzyl)-1H-pyrazolo[3,4-b]pyridine

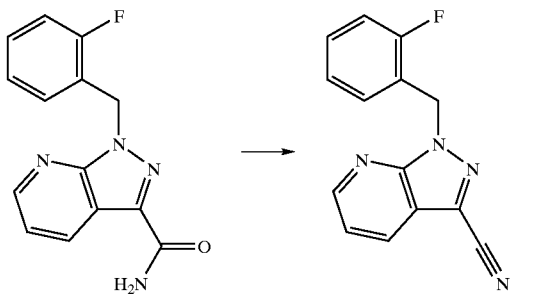

36.1 g (133 mmol) of 1-(2-fluorobenzyl)-1H-pyrazolo[3,4-b]pyridine-3-carboxamide from Example 22A are dissolved in 330 ml of THF and mixed with 27 g (341 mmol) of pyridine. Over a period of 10 min, 47.76 ml (71.66 g, 341 mmol) of trifluoroacetic anhydride are subsequently added, and the temperature increases to 40° C. during the addition. The mixture is stirred at room temperature overnight. The mixture is subsequently poured into 1 l of water, and the mixture is extracted three times with 0.5 l of ethyl acetate each time. The organic phase is washed with saturated sodium bicarbonate solution and with 1 N HCl, dried with MgSO$_4$ and concentrated using a rotary evaporator.

Yield: 33.7 g (100% of theory). M.p.: 81° C. Rf (SiO$_2$, T1E1): 0.74.

Example 24A

Methyl 1-(2-Fluorobenzyl)-1H-pyrazolo[3,4-b]pyridine-3-carboximidate

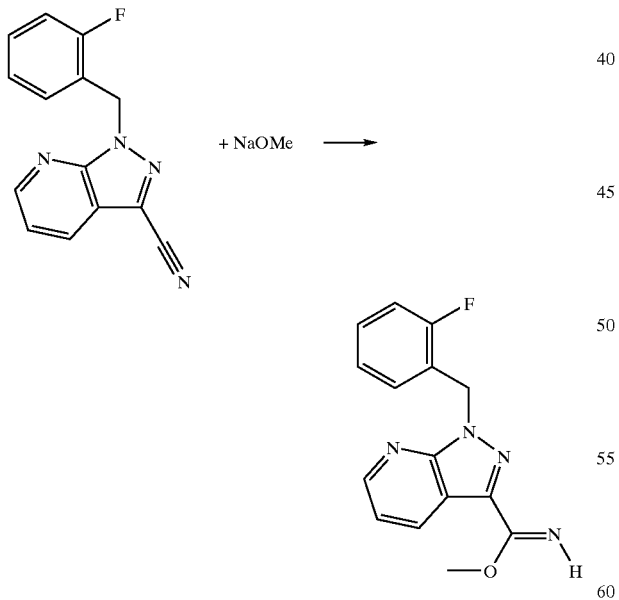

30.37 g (562 mmol) of sodium methoxide are dissolved in 1.5 l of methanol, and 36.45 g (144.5 mmol) of 3-cyano-1-(2-fluorobenzyl)-1H-pyrazolo[3,4-b]pyridine from Example 23A are added. The mixture is stirred at room temperature for 2 hours and the resulting solution is directly employed in the next step.

Example 1-(2-Fluorobenzyl)-1H-pyrazolo[3,4-b]pyridine-3-carboxamidine

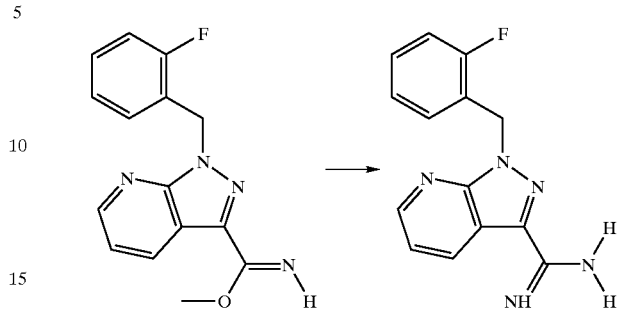

The above solution of methyl (2-fluorobenzyl)-1H-pyrazolo[3,4-b]pyridine-3-carboximidate from Example 24A in methanol is admixed with 33.76 g (32.19 ml, 562 mmol) of glacial acetic acid and 9.28 g (173 mmol) of ammonium chloride, and the mixture is stirred under reflux overnight. The solvent is evaporated off under reduced pressure, the residue is triturated well with acetone and the precipitated solid is filtered off with suction. The product is added to 2 l of water, the mixture is admixed with stirring with 31.8 g of sodium carbonate and extracted three times with a total of 1 l of ethyl acetate, and the organic phase is dried with magnesium sulphate and concentrated under reduced pressure.

Yield: 27.5 g (76.4% of theory over two steps). M.p.: 86° C. Rf (SiO$_2$, T1EtOH1): 0.08.

Preparation Examples

Example 1

3-(4-Amino-5-methylsulphonylpyrimidin-2-yl)-1-(2-fluorobenzyl)-1H-pyrazolo[3,4-b]pyridine

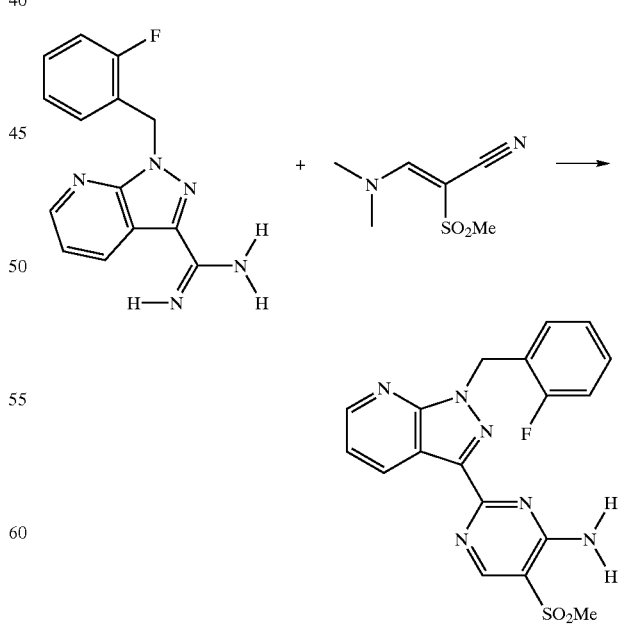

2 g (7.42 mmol) of 1-(2-fluorobenzyl)-1H-pyrazolo[3,4-b]pyridine-3-carboxamidine from Example 25A, 1.39 g (7 mmol) of 3-(dimethylamino)-2-(methylsulphonyl)-2-acrylonitrile (which can be prepared analogously to Example 1A), 0.79 ml (7 mmol) of piperidine and 200 ml of isoamyl alcohol are stirred at 110° C. for 12 h. After cooling, the precipitated crystals are filtered off with suction and washed with diethyl ether. This gives 0.94 g (31.8% of theory) of the title compound.

M.p.: 272° C. Rf (SiO$_2$, EE): 0.72.

The following compounds were prepared analogously:

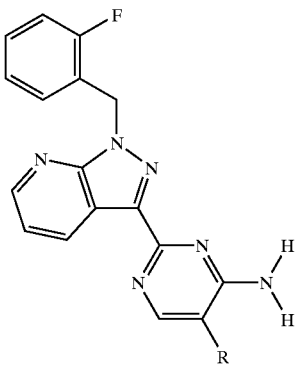

| Ex. No. | R | M.p. [° C.] | Rf (SiO$_2$) | Yield |
|---|---|---|---|---|
| 2 | CH$_3$CH$_2$CH$_2$SO$_2$— | 254 | 0.87 (EA) | 30 |
| 3 | (CH$_3$)$_2$CHSO$_2$— | 268 | 0.83 (EA) | 31.6 |
| 4 | (CH$_3$)$_3$C—SO$_2$— | >280 | 0.24 (T1E1) | 25.4 |
| 5 | [(CH$_3$)$_2$CHO]$_2$PO— | 190 | 0.19 (T1E1) | 10.8 |
| 6 | —CONH$_2$ | 215 | 0.25 (T1E1) | 9.6 |
| 7 | —SO$_2$-(2-thienyl) | 275 | 0.48 (T1E1) | 11.5 |
| 8 | —CH$_2$CF$_3$ | 181 | | 14.4 |
| 9 | PhSO$_2$— | 279 | 0.51 (T1E1) | 29.2 |
| 10 | PhSO— | 218 | 0.26 (T1E1) | 19.4 |
| 11 | —(CH$_2$)$_5$CN | 107 | 0.22 (EA) | 18 |
| 12 | —(CH$_2$)$_7$CN | 147 | 0.36 (EA) | 13.5 |
| 13 | —CH$_2$CH$_2$—CN | 201 | 0.2 (T4EtOH1) | 12 |

The corresponding 3-dimethylaminoacrylonitriles where the respective substituent R is in the 2-position, which are to be reacted, as starting materials of Examples 2 to 13, with the amidine 24A, can be prepared analogously to Examples 1A and 3A.

Example 14

3-[5-Cyano-4-(4-methylphenyl)pyrimidin-2-yl]-1-(2-fluorobenzyl)-1H-pyrazolo[3,4-b]pyridine

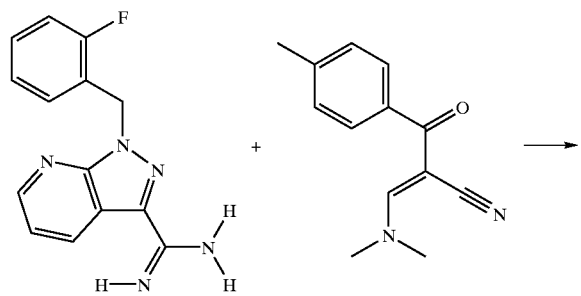

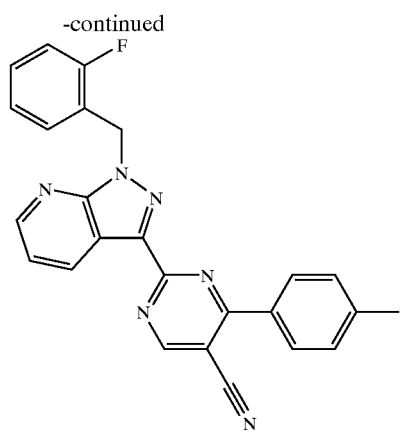

At 110° C., 200 mg (0.74 mmol) of 1-(2-fluorobenzyl)-1H-pyrazolo[3,4-b]pyridine-3-carboxamidine from Example 25A, 171 mg (0.8 mmol) of (dimethylamino)-2-(4-methylbenzoyl)-2-acrylonitrile (which can be prepared analogously to Example 1), 0.68 mg (0.8 mmol) of piperidine and 20 ml of 2-pentanol are stirred for 12 h. After cooling, the solvent is evaporated under reduced pressure and the residue is chromatographed over silica gel. This gives 217 mg (69.5% of theory) of the title compound.

M.p.: 229° C.

Example 15

3-(4,6-Diamino-5-benzylpyrimidin-2-yl)-1-(2-fluorobenzyl)-1H-pyrazolo[3,4-b]pyridine

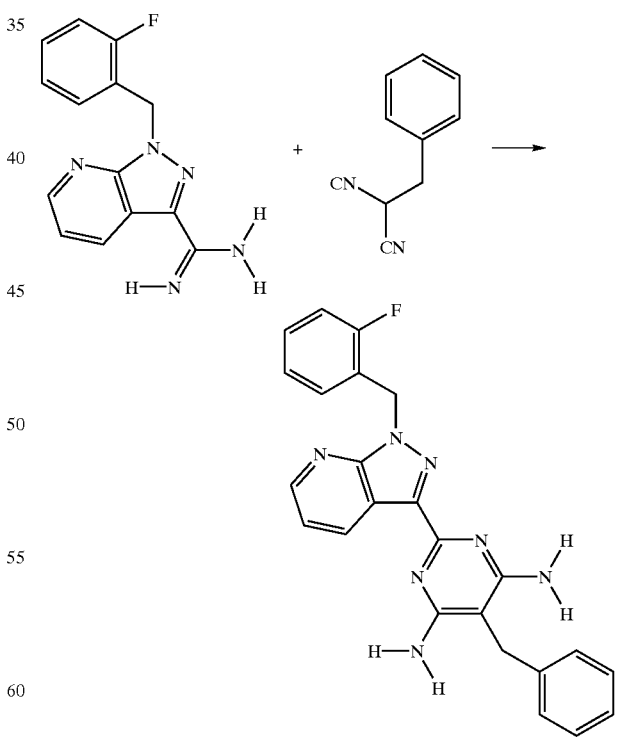

At 110° C., 200 mg (0.74 mmol) of 1-(2-fluorobenzyl)-1H-pyrazolo[3,4-b]pyridine-3-carboxamidine from Example 25A, 125 mg (0.8 mmol) of 2-benzylmalonodinitrile (preparable from malonodinitrile and benzyl bromide using a base such as potassium

Example 16

3-(4,6-Diamino-5-N-morpholinopyrimidin-2-yl)-1-(2-fluorobenzyl)-1H-pyrazolo[3,4-b]pyridine

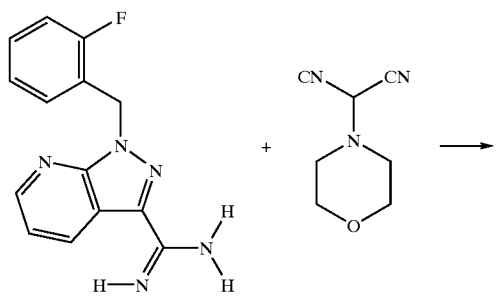

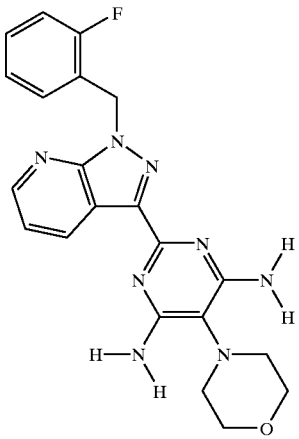

At 105° C., 200 mg (0.74 mmol) of 1-(2-fluorobenzyl) 1H-pyrazolo[3,4-b]pyridine-3-carboxamidine from Example 25A and 400 mg (2.65 mmol) of 2-N-morpholinomalonodinitrile (for the synthesis cf. H. Gold and O. Bayer, Chem. Ber. 1961, 94, 2594) are heated under reduced pressure for 12 h. The solid residue is dissolved in DMF, silica gel is added and the solvent is evaporated under reduced pressure. Chromatography gives 222 mg (71.1% of theory) of the title compound.

M.p.: 261° C. Rf: (EA): 0.2.

The following compounds were prepared analogously:

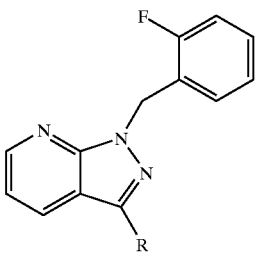

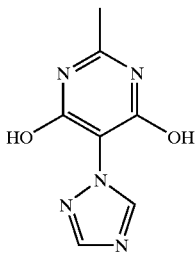

| Ex. No. | R | Yield | Rf (SiO$_2$) |
|---|---|---|---|
| 17 (from 25A and diethyl 2-(1H-1,2,4-triazolyl)-malonate (preparable analogously to Example 7A)) | (structure shown) | 29.5 | 0.32 (BABA) | carbonate), 0.68 mg (0.8 mmol) of piperidine and 20 ml of 2-pentanol are stirred for 12 h. After cooling, the solvent is evaporated under reduced pressure and the residue is chromatographed over silica gel. This gives 165 mg (52.2% of theory) of the title compound.

M.p.: 193° C.

-continued
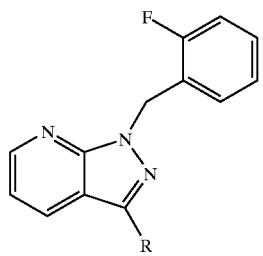
| Ex. No. | R | | Rf (SiO₂) |
|---|---|---|---|
| 18 (from 25A and 10A) | 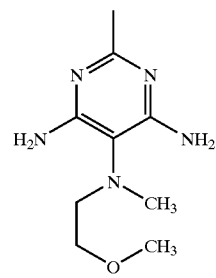 | 11.9 | 0.36 (BABA) |
| 19 (from 25A and ethyl) 2-acetamidocyano-acetate (commercially available)) | 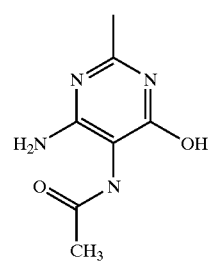 | 12.9 | 0.61 (BABA) |
| 20 (from 25A and diethyl 2-N-pyrrolomalonate (commercially available)) | 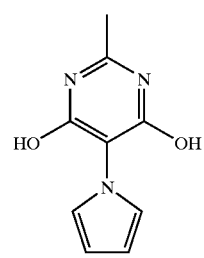 | 15.2 | 0.63 (EA) |
| | | Yield (% of theory) | |
|---|---|---|---|
| 21 (From 25A and 8A) | 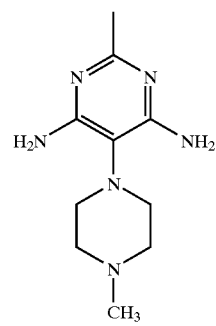 | 82.7 | 0.07 (BABA) |

-continued

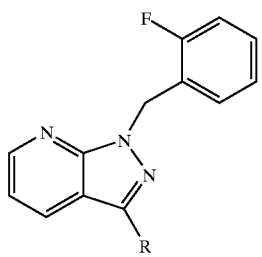

| Ex. No. | R | | Rf (SiO$_2$) |
|---|---|---|---|
| 22 (from 25A and hydroxyimino-malonitrile, sodium salt (commercially available)) | H$_2$N–[pyrimidine with 2-CH$_3$, 4,6-(NH$_2$)$_2$, 5-N=O]–NH$_2$ | 1.8 | 0.50 (EA) |
| 23 (from 25A and 12A) | [2-methyl-4,6-diamino-5-(thiomorpholin-4-yl)pyrimidine] | 43.3 | 0.85 (BABA) |
| 24 (from 25A and 13A) | [2-methyl-4,6-diamino-5-(2,6-dimethylmorpholin-4-yl)pyrimidine] | 72.4 | 0.72 (BABA) |
| 25 (from 25A and 2-N-dimethylaminomalo-nodinitrile (for the synthesis, cf. Chem. Ber. 1961, 94, 2594)) | [2-methyl-4,6-diamino-5-(N,N-dimethylamino)pyrimidine] | 41.6 | 0.52 (BABA) |
| 26 (from 25A and 2-N-diethylaminomalono-dinitrile (for the synthesis, cf. Chem. Ber. 1961, 94, 2594)) | [2-methyl-4,6-diamino-5-(N,N-diethylamino)pyrimidine] | 58.4 | 0.75 (BABA) |

-continued
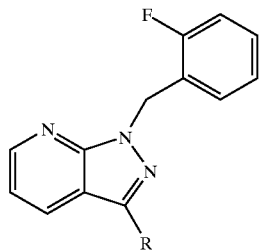
| Ex. No. | R | | Rf (SiO$_2$) |
|---|---|---|---|
| 27 (from 25A and 14A) | (structure) | 52.3 | 0.27 (BABA) |
| 28 (from 25A and 9A) | (structure) | 54.8 | 0.65 (BABA) |
| 29 (from 25A and 15A) | (structure) | 55.1 | 0.48 (BABA) |
| 30 (from 25A and 16A) | (structure) | crude | 0.08 (BABA) |

-continued
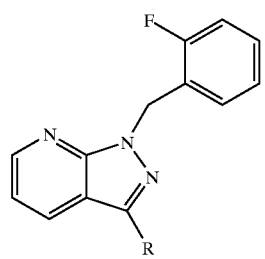
| Ex. No. | R | | Rf (SiO$_2$) |
|---|---|---|---|
| 31 (from 25A and 17A) | 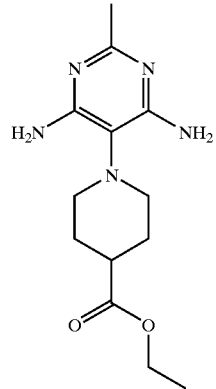 | 35.3 | 0.50 (EA) |
| 32 (from 25A and 18A) | 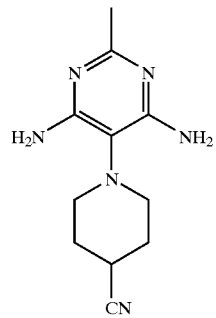 | 97.7 | 0.53 (BABA) |
| 33 (from 25A and 2-(thiazol-2-yl)-malonodinitrile (Synthese: Heterocycles, 1990, 31, 1115) | 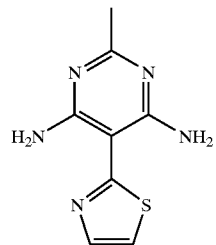 | 22.1 | 0.85 (BABA) |
| 34 (from 25A and 19A) | 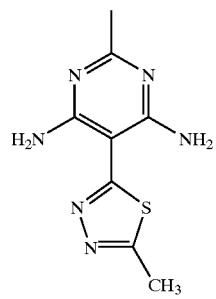 | 1.2 | 0.63 (BABA) |

| Ex. No. | R | | Rf (SiO$_2$) |
|---|---|---|---|
| 35 (from 25A and 2-methylsulphonyl-malonodinitrile) | 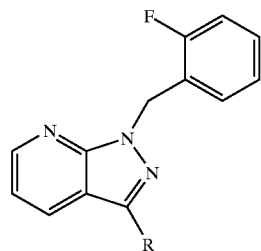 | 11.3 | 0.90 (BABA) |

Example 36

3-(4,6-bis(Trifluoromethyl)-pyrimidin-2-yl)-1-(2-fluorobenzyl)1H-pyrazolo[3,4-b]pyridine

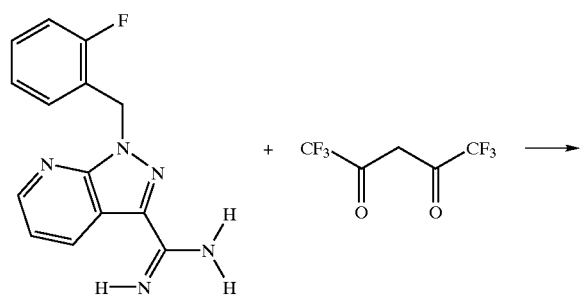

At 110° C., 50 mg (19 mmol) of 1-(2-fluorobenzyl)-1H-pyrazolo[3,4-b]pyridine-3-carboxamidine from Example 25A and 42 mg (20 mmol) of 1,1,1,5,5,5-hexafluoroacetylacetone are heated for 5 h. Chromatography gives 33 mg (40.3% of theory) of the title compound.

M.p.: 109° C. Rf: (toluene): 0.35.

Example 37

3-(5-Ethoxycarbonyl-4-trifluoromethyl-pyrimidin-2-yl)-1-(2-fluorobenzyl)-1H-pyrazolo[3,4-b]pyridine

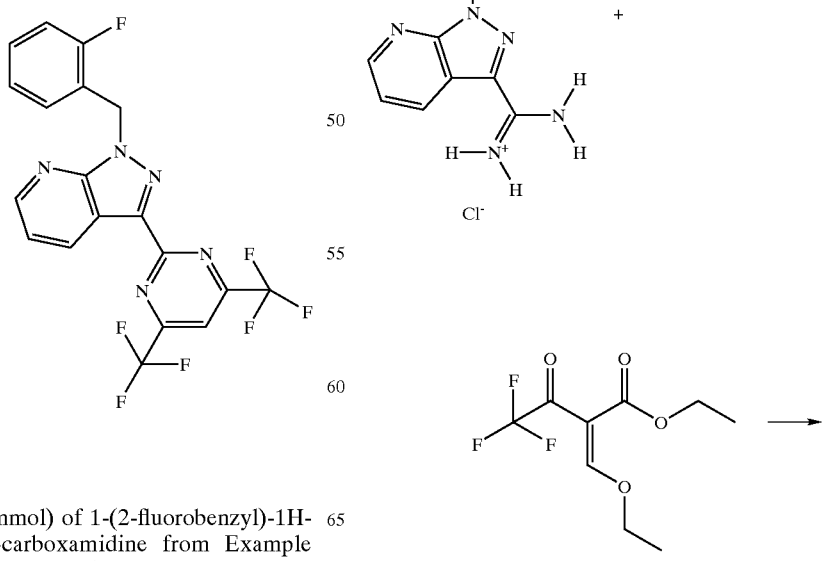

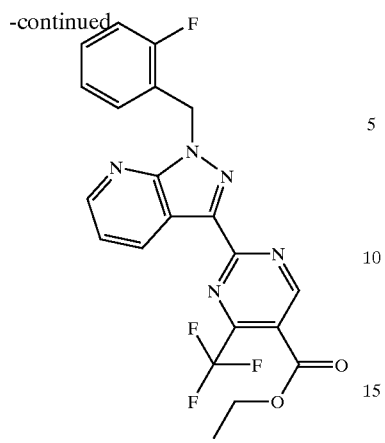

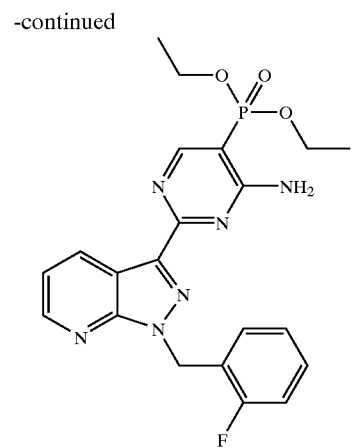

600 mg of the crude 1-(2-fluorobenzyl)1H-pyrazolo[3,4-b]pyridine-3-carboxamidine hydrochloride (preparable from the amidine 25A by reaction with HCl) are stirred in 30 ml of methanol with 106 mg of sodium methoxide and admixed with 472 mg (1.96 mmol) of ethyl 3-ethoxy-2-trifluoroacetyl-acrylate. The mixture is boiled for 12 hours and the precipitate is then filtered off with suction and washed with ether. This gives 249 mg (27.5% of theory) of crystals.

M.p.: 174° C. Rf: SiO$_2$ T1E1: 0.76.

2.44 g (9.00 mmol) of the amidine from Example 25A and 3.71 g (16.0 mmol) of diethyl 1-cyano-1-(dimethylamino)methylene-methanephosphonate (Aboujaoude, Elie Elia; Collignon, Noel; Savignac, Philippe, Tetrahedron, 41, 1985, 427–434) were mixed well, treated for 5 minutes with ultrasound and subsequently stirred at 100° C. under reduced pressure (membrane pump) overnight. The mixture was cooled to room temperature, stirred with hot methanol and freed from insoluble components by filtration. The filtrate was concentrated and chromatographed over silica gel (C→C:E 1:1→E).

| Yield: | 638 mg (16%) |
| M.p.: | 185° C. |
| R$_f$-value: | 0.09 (C:E 1:1) |

Example 38

Diethyl 4-Amino-2-{1-(2-fluorobenzyl)-1H-pyrazolo[3,4-b]pyridin-3-yl}-pyrimidine-5-phosphonate

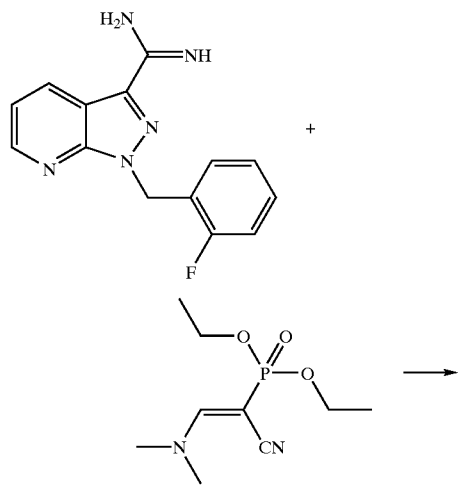

Example 39

3-(4-Amino-5-N-morpholino-pyrimidin-2-yl)-1-(2-fluorobenzyl)-1H-pyrazolo[3,4-b]pyridine

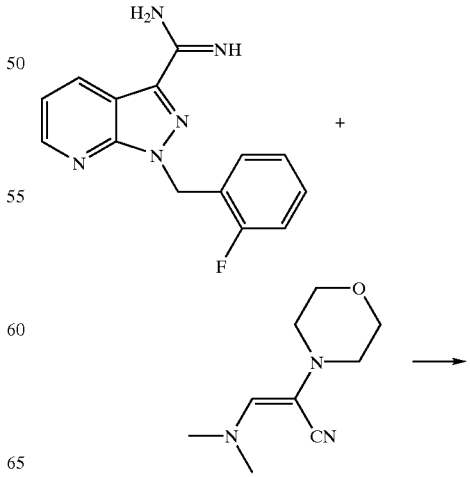

-continued

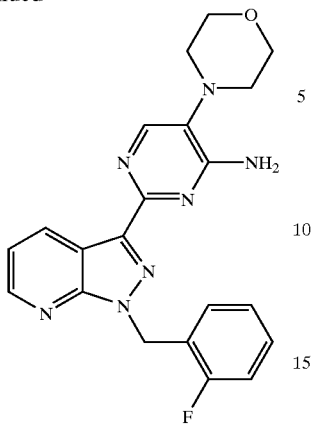

1.00 g (3.72 mmol) of the amidine from Example 25A and 2.00 g (11.0 mmol) of 3-(dimethylamino)-2-morpholino-acrylonitrile from Example 3A were mixed well, treated with ultrasound for 5 minutes and subsequently stirred at 120° C. under reduced pressure (membrane pump) overnight. The mixture was cooled to room temperature and stirred with tert-butyl methyl ether, and the resulting precipitate was filtered off with suction and chromatographed over silica gel (C:E 100:1→C:E 1:1).

| Yield: | 262 mg (17%) |
| M.p.: | 205° C. |
| $R_f$-value: | 0.05 (C:E 1:1) |

Example 40

3-(4-Amino-5-N-thiomorpholino-pyrimidin-2-yl)-1-(2-fluorobenzyl)-1H-pyrazolo[3,4-b]pyridine

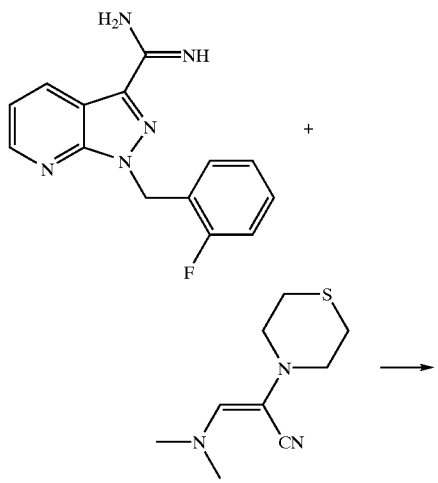

-continued

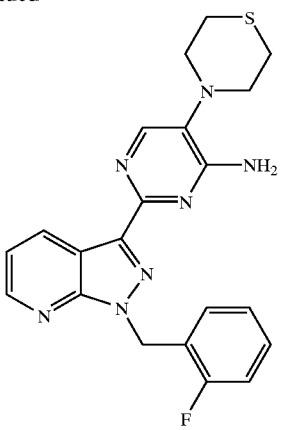

5.00 g (18.6 mmol) of the amidine from Example 25A and 9.98 g (50.7 mmol) of 3-(dimethylamino)-2-thiomorpholinoacrylonitrile from 4A were mixed well, treated with ultrasound for 5 minutes and subsequently stirred at 100° C. under reduced pressure (membrane pump) overnight. The mixture was cooled to room temperature and stirred with tert-butyl methyl ether, and the resulting precipitate was filtered off with suction.

| Yield | 1.43 g (18%) |
| M.p.: | >250° C. |
| $R_f$-value: | 0.06 (C:EE 1:1) |

Example 41

3-(4-Hydroxy-5-(methylsulphonyl)-pyrimidin-2-yl)-1-(2-fluorobenzyl)-1H-pyrazolo[3,4-b]pyridine

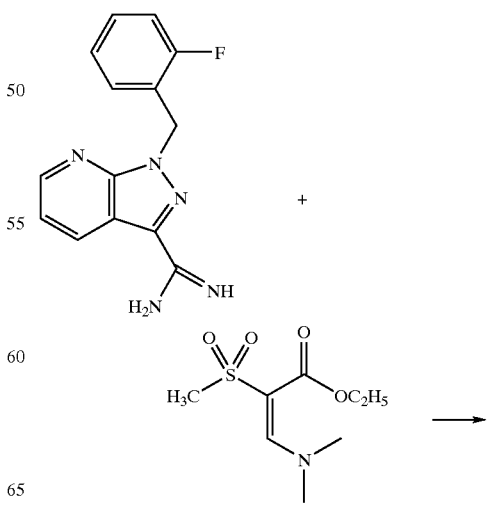

hours. The residue is cooled, digested with toluene and filtered, and the filtrate is washed with toluene.

Yield: 1.16 g (33.6% of theory). Rf (SiO$_2$, EA): 0.23.

Example 42

3-(6-Chloro-8-methyl-9H-purin-2-yl)-1-(2-fluorobenzyl)-1H-pyrazolo[3,4-b]pyridine

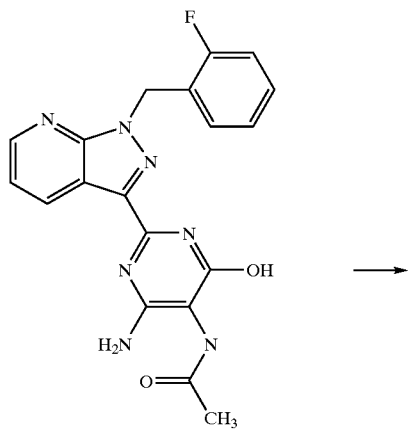

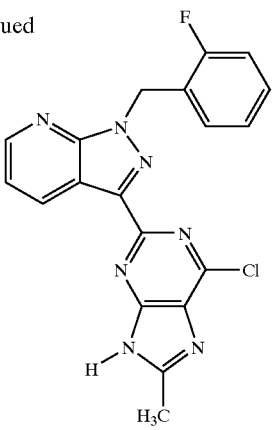

650 mg (1.65 mmol) of the hydroxypyrimidine from Example 19 are taken up in 3 ml of phosphorus oxytrichloride, two drops of N,N-dimethylaniline are added, and the solution is heated at reflux for three hours. The reaction mixture is cooled and concentrated using a rotary evaporator. The residue is taken up in ethyl acetate, washed carefully with saturated sodium bicarbonate solution, dried and concentrated using a rotary evaporator. The crude product is reacted further.

Yield: 580 mg (89.1% of theory). Rf (SiO$_2$, EA): 0.21.

The following compounds were prepared analogously to the preparation of Example 42:

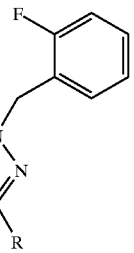

| Ex No. | Starting material | Product | Yield (% of theory) | Rf (SiO$_2$) |
|---|---|---|---|---|
| 43 | 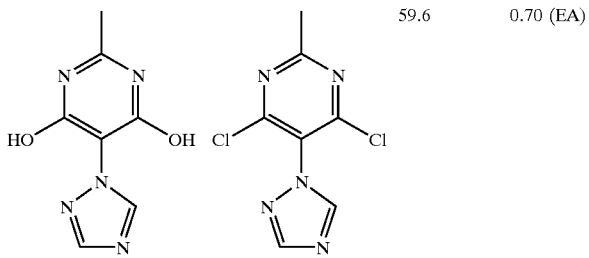 | | 59.6 | 0.70 (EA) |

-continued

| Ex No. | Starting material | Product | Yield (% of theory) | Rf (SiO$_2$) |
|---|---|---|---|---|
| 44 | | | not determined (crude product) | 0.65 (C1E1) |
| 45 | | | 21.4 | 0.45 (C1E2) |

The starting material from Example 43 was prepared as Example 17. The starting material from Example 44 was prepared as Example 20. The starting material from Example 45 was prepared as Example 41.

Example 46

3-(5-Ethyl-4-(2-hydroxyethylaminocarbonyl)pyrimidin-2-yl)-1-(2-fluorobenzyl)-1H-pyrazolo[3,4-b]pyridine

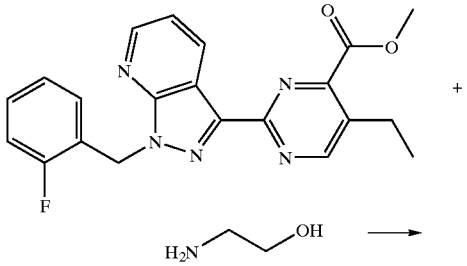

-continued

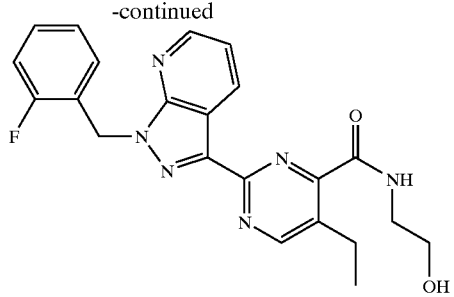

70.0 mg (0.179 mmol) of the methylester (prepared from 25A and methyl 4-(dimethylamino)-3-ethyl-2-oxo-3-butenoate analogously to Example 36) are dissolved in 109.3 mg (1.78 mmol) of the amine, and the mixture is stirred at 60° C. for 3 hours. Dichloromethane is added, and the mixture is washed once with a 0.5N hydrochloric acid solution. The organic phase is dried with magnesium sulphate and concentrated under reduced pressure. Yield: 30.6 mg (40.7% of theory).

Rf (SiO$_2$, E) 0.31.

The following compounds were prepared in an analogous manner by reaction with the appropriate amines:

| Ex. No. | R | Yield | Rf (SiO₂) |
|---|---|---|---|
| 47 | cyclopropyl-NH- | 36.0 | 0.48 (C1E2) |
| 48 | morpholinyl | 13.2 | 0.20 (C1E2) |
| 49 | -N(CH₃)₂ | crude | 0.12 (C1E2) |
| 50 | 2,6-dimethylmorpholinyl | 22.0 | 0.37 (C1E2) |
| 51 | pyrrolidinyl | crude | 0.42 (E) |
| 52 | 4-hydroxypiperidinyl | 22.8 | 0.05 (C1E2) |
| 53 | -NH-CH₂CH₂CH₂-O-CH₂CH₃ | crude | 0.37 (C1E2) |
| 54 | -NH-CH₂-Ph | crude | 0.61 (C1E2) |
| 55 | -NH-CH₂-cyclopropyl | 87.0 | 0.65 (C1E2) |
| 56 | -NH-CH₂-furyl | 57.7 | 0.66 (C1E2) |
| 57 | —NH₂ | 86.9 | 0.26 (C1E2) |

The amines which are to be used as starting materials are in each case commercially available or obtainable in a simple manner by standard methods known to the person skilled in the art, such as those described, for example, in J. March, Advanced Organic Chemistry, 3rd ed., Wiley, 1985, p. 1153 f.

Example 58

3-(4-(4,5-Dihydro-1H-imidazol-2-yl)-5-ethyl-pyrimidin-2-yl)-1-(2-fluorobenzyl)-1-pyrazolo[3,4-b]pyridine

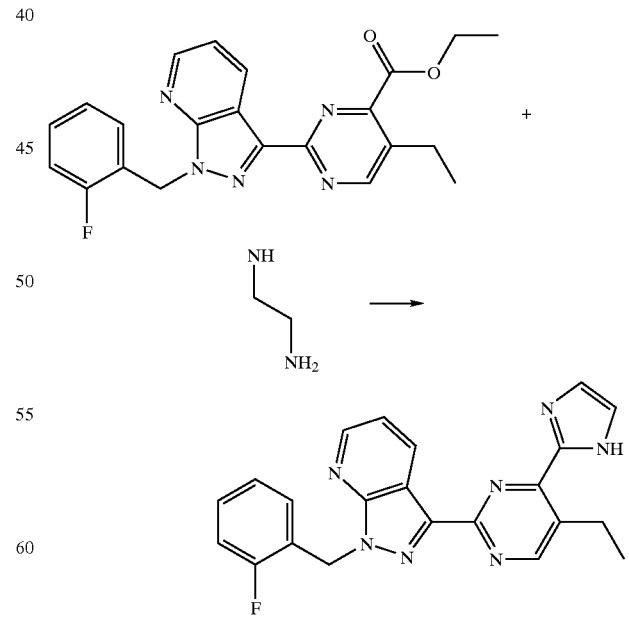

68.9 mg (1.15 mmol) of ethylenediamine are dissolved in 10 ml of toluene, 0.60 ml (1.15 mmol) of a 2M solution of trimethylaluminium and toluene are added at 0° C., and the mixture is stirred at room temperature for 2 hours. 155 mg (0.38 mmol) of the ethyl ester (prepared from 25A and ethyl 4-(dimethylamino)-3-ethyl-2-oxo-3-buteneoate analogously to Example 36) are then added. The mixture is stirred at 75° C. for five days, cooled and washed once with sodium potassium tartrate solution, and the aqueous phase is extracted once with dichloromethane. The combined organic phases are dried with magnesium sulphate, admixed with 500 mg of silica gel and concentrated using a rotary evaporator.

For purification, the substance is chromatographed over 10 g of silica gel 60 (particle size 0.040–0.063 mm) using ethyl acetate to ethyl acetate/methanol 9:1 as mobile phase. Yield 75.0 mg (49% of theory).

Rf (SiO$_2$, C1E1): 0.04.

Example 59

3-[5-Ethyl-4-(1H-imidazol-2-yl)-pyrimidin-2-yl]-1-(2-fluorobenzyl)-1H-pyrazolo[3,4-b]pyridine

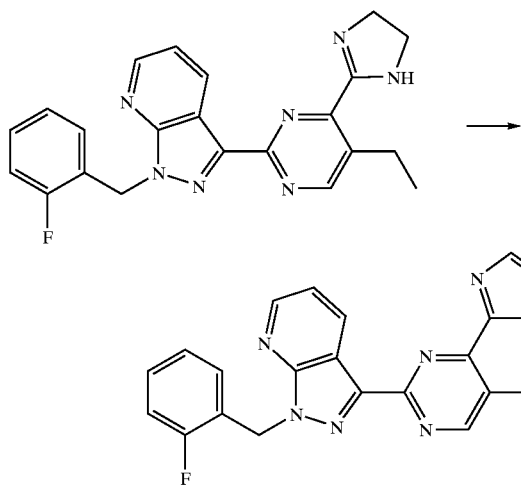

62 mg (0.15 mmol) of the dihydroimidazole from Example 58 and 100 mg of palladium/carbon (10%) are heated to reflux in 5 ml of toluene. After 6 days, the mixture is filtered off and the solvent is evaporated under reduced pressure.

For purification, the substance is chromatographed over 8 g of silica gel 60 (particle size 0.040–0.063 mm) using cyclohexane/ethyl acetate 2:1 to 1:2 as mobile phase.

Yield: 8.8 mg (14.3% of theory). Rf (SiO$_2$, C1E2): 0.24.

Example 60

3-(5-Ethyl-4-(1H-imidazol-1-yl)-pyrimidin-2-yl)-1-(2-fluorobenzyl)-1H-pyrazolo[3,4-b]pyridine

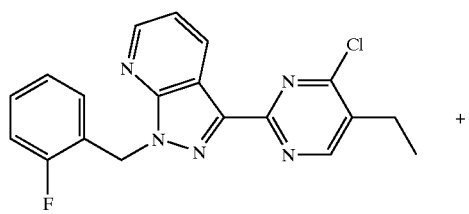

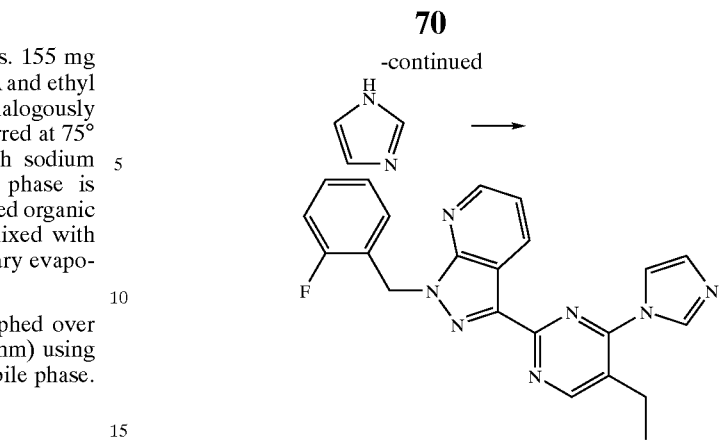

60 mg (0.16 mmol) of the chloro compound (prepared from 25A and ethyl 2-formylbutanoate analogously to Example 36 and subsequent reaction with phosphorus oxytrichloride analogously to Example 42) and 22.2 mg (0.33 mmol) of imidazole are dissolved in 5 ml of dimethylformamide and admixed with 33.8 mg (0.24 mmol) of potassium carbonate. The mixture is stirred at 100° C. overnight. The mixture is cooled, diluted with ethyl acetate and washed twice with water. The organic phase is dried using magnesium sulphate and concentrated under reduced pressure. Yield: 47.4 mg (72.7% of theory).

Analogously to Example 60, the following compounds were prepared by reaction with the appropriate amines:

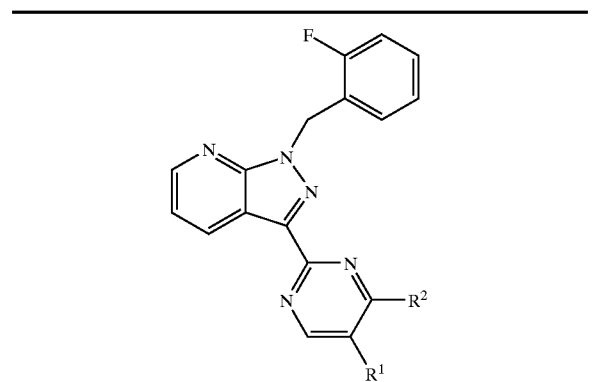

| Ex. No. | R$^1$ | R$^2$ | Yield | Rf (SiO$_2$) |
|---|---|---|---|---|
| 61 (from 45) | SO$_2$CH$_3$ | —N(morpholine) | 79.3 | 0.58 (E) |
| 62 (from 45) | SO$_2$CH$_3$ | —NH—CH$_2$CH$_2$—CH$_3$ | 58.3 | 0.34 (C1E2) |
| 63 (from 45) | SO$_2$CH$_3$ | —NH-cyclopropyl | 29.0 | 0.43 (C1E2) |
| 64 (see Ex. 60) | CH$_2$CH$_3$ | —NH—CH$_2$CH$_2$—CH$_3$ | 25.6 | 0.18 (C1E2) |

-continued

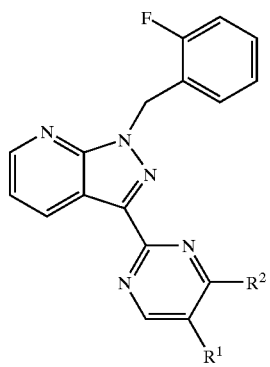

| Ex. No. | R¹ | R² | Yield | Rf (SiO₂) |
|---|---|---|---|---|
| 65 (see Ex. 60) | CH₂CH₃ | N-methyl-N-cyclopropylamino | 11.4 | 0.11 (C1E2) |
| 66 (see Ex. 60) | CH₂CH₃ | piperidin-1-yl | crude | 0.36 (C1E2) |
| 67 (see Ex. 60) | CH₂CH₃ | morpholin-4-yl | crude | 0.22 (C1E2) |
| 68 (see Ex. 60) | CH₂CH₃ | pyrrolidin-1-yl | crude | 0.14 (C1E2) |

-continued

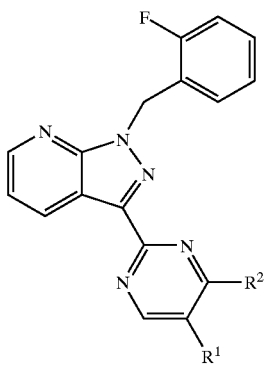

| Ex. No. | R¹ | R² | Yield | Rf (SiO₂) |
|---|---|---|---|---|
| 69 (see Ex. 60) | CH₂CH₃ | N-methylguanidino | 7.7 | 0.03 (C1E2) |
| 70 (see Ex. 60) | CH₂CH₃ | N,N-dimethylamino | 8.8 | 0.30 (C1E2) |

Examples 71–79

The chlorine group of the compounds of Examples 42 to 45 can be reduced by known methods using ammonium formate and palladium/carbon, or be exchanged by reaction with nucleophiles such as the azide anion, ammonia, amines or methanol. The azide group introduced in this manner can in turn be reduced with sodium dithionite. In this manner, the following compounds are obtained:

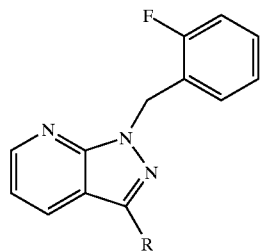

| Ex. No. | R | Yield (% of theory) | Rf (SiO₂) |
|---|---|---|---|
| 71 (from 42) | 2-methyl-8-methyl-purin-9-yl | 53.7 | 0.25 (EA) |

-continued
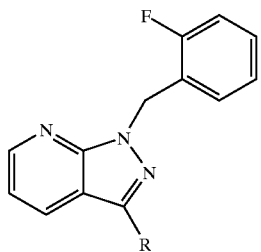
| Ex. No. | R | Yield (% of theory) | Rf (SiO$_2$) |
|---|---|---|---|
| 72 (from 42) | 2-methyl-8-methyl-6-azido-purin-9-yl | 26.8 | 0.69 (BABA) |
| 73 (from 42) | 2-methyl-8-methyl-6-amino-purin-9-yl | 13.8 | 0.61 (BABA) |
| 74 (from 42) | 2-methyl-8-methyl-6-(n-butylamino)-purin-9-yl | crude | 0.78 (BABA) |
| 75 (from 44) | 2-methyl-4-amino-6-chloro-5-(pyrrol-1-yl)pyrimidine | crude | 0.53 (BABA) |
| 76 (from 44) | 2-methyl-4,6-bis(n-butylamino)-5-(pyrrol-1-yl)pyrimidine | crude | 0.77 (EA) |

-continued
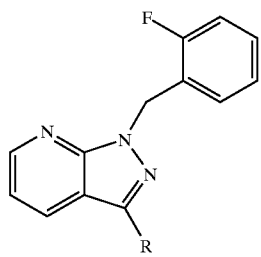
| Ex. No. | R | Yield (% of theory) | Rf (SiO$_2$) |
|---|---|---|---|
| 77 (from 43) | | 9.8 | |
| 78 (from 43) | | 10.6 | 0.73 (BABA) |
| 79 (from 43) | | 18.9 | 0.29 (EA) |

Example 80

3-(4-Diacetylamino-5-ethyl-pyrimidin-2-yl)-1-(2-fluorobenzyl)-1H-pyrazolo[3,4-b]pyridine

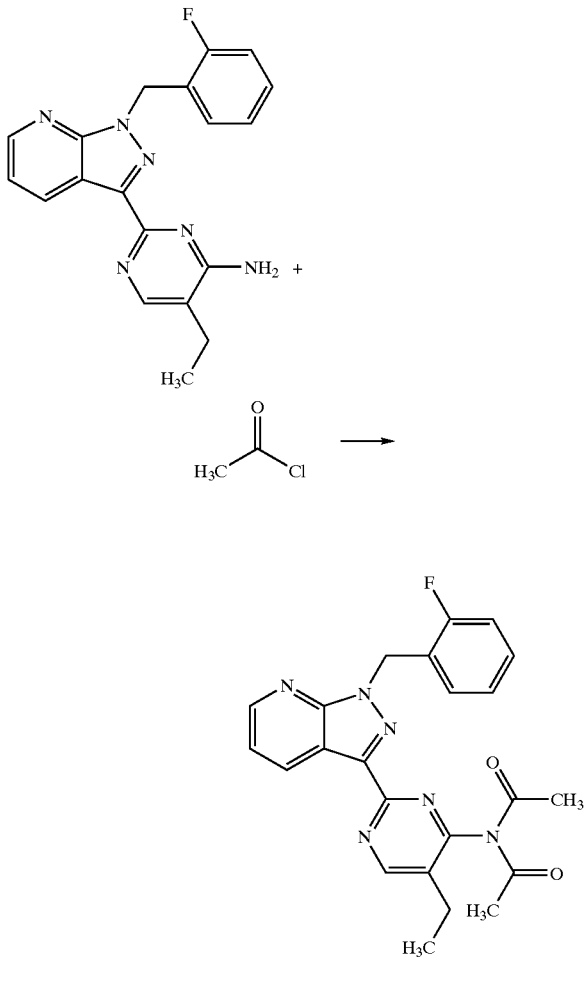

50.0 mg (0.14 mmol) of the amine (preparable analogously to Example 60 by reaction of the chlorocompound described therein with ammonia or with sodium azide and subsequent reduction with sodium dithionide) are dissolved in dichloromethane and admixed with 33.8 mg (0.43 mmol) of acetyl chloride and 68.1 mg (0.86 mmol) of pyridine. The solution is stirred at RT for 4 hours, washed once with 1N HCl and then with saturated NaHCO$_3$ solution. The organic phase is dried using magnesium sulphate and concentrated under reduced pressure. For purification, the substance was chromatographed over silica gel 60 (particle size 0.040–0.063 mm) using cyclohexane/ethyl acetate 1:1 as mobile phase. Yield: 33.2 mg (53.5% of theory).

Rf (SiO$_2$, C1E2): 0.41.

Example 81

3-[4-(2-Benzoyloxymethylbenzoylamino)-5-ethylpyrimidin-2-yl]-1-(2-fluorobenzyl-1H-pyrazolo[3,4-b]pyridine

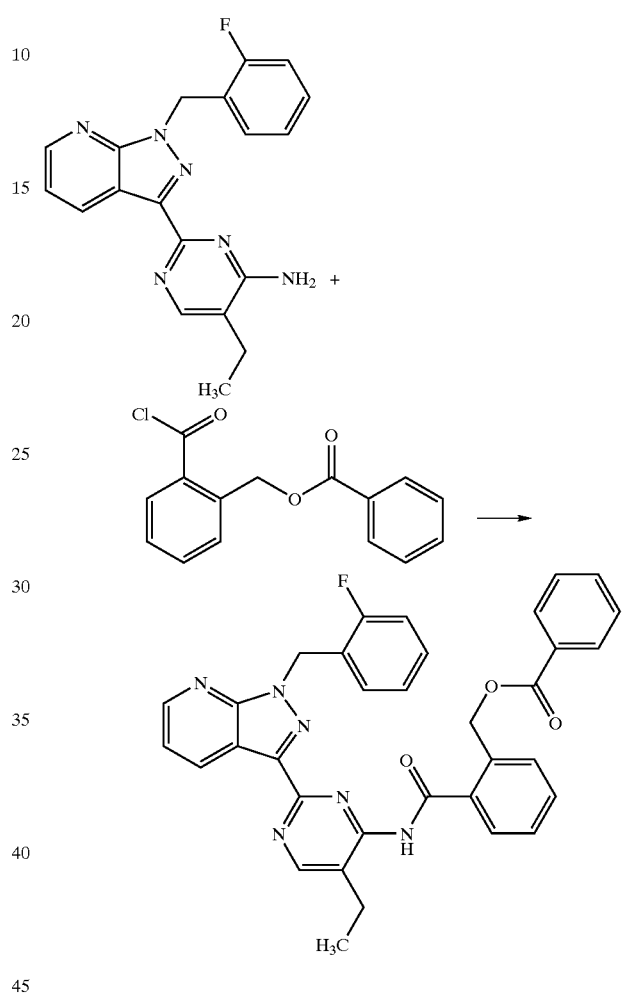

At room temperature, 9 mg (0.23 mmol) of sodium hydride (60% strength suspension in oil) are suspended in 1 ml of tetrahydrofuran (THF). A solution of 40 mg (0.11 mmol) of the amine (cf. Example 80) in 0.8 ml of THF is added, and a solution of 34.7 mg (0.13 mmol) of 2-(benzoyloxymethyl)benzoyl chloride is then added. After 30 min, another 5 ml (0.12 mmol) of sodium hydride (60% strength) and 14 mg (0.05 mmol) of the abovementioned acyl chloride are added. After 1 h, the mixture is admixed with water and extracted with ethyl acetate, and the organic phase is washed with 1 M hydrochloric acid and saturated NaHCO$_3$ solution, dried with magnesium sulphate and concentrated under reduced pressure. The substance is recrystallized from cyclohexane/ethyl acetate.

Yield: 25 mg (37.1% of theory). Rf (SiO$_2$, C1E1): 0.50.

Example 82

3-(4-Acetoxy-5-ethyl-pyrimidin-2-yl)-1-(2-fluorobenzyl)-1H-pyrazolo[3,4-b]pyridine and 3-(3-Acetyl-5-ethyl-pyrimidin-4-on-2-yl)-1-(2-fluorobenzyl)-1H-pyrazolo[3,4-b]pyridine

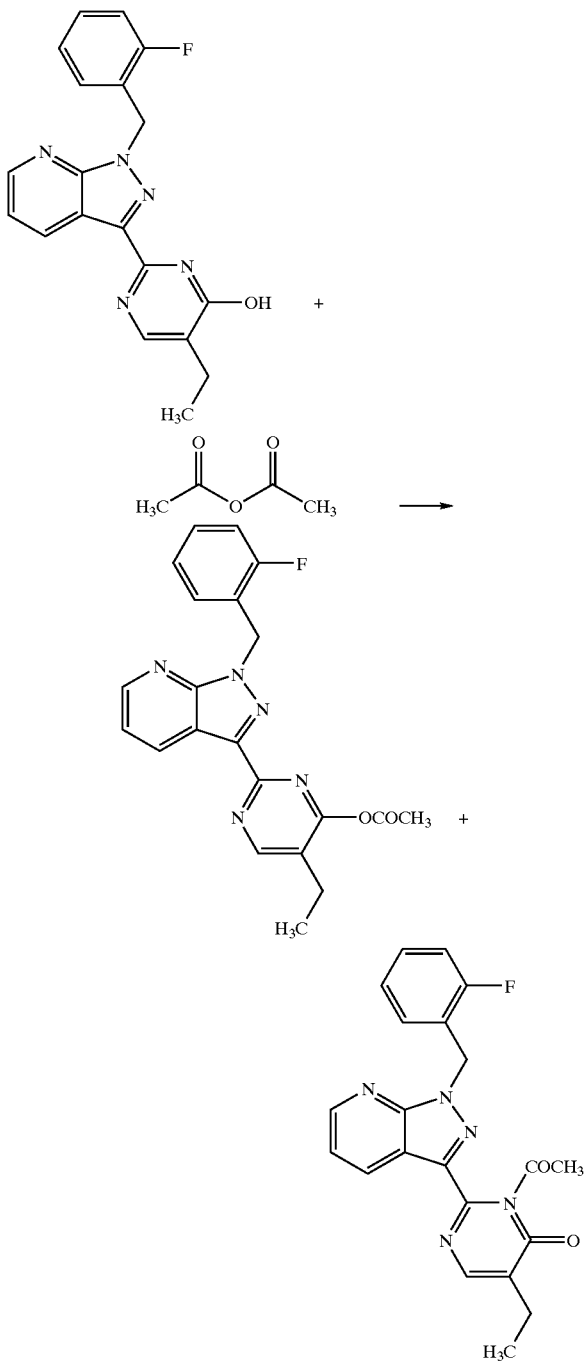

73.8 mg (0.21 mmol) of the hydroxypyrimidine compound (prepared from 25A and ethyl 2-formylbutanoate analogously to Example 36) are dissolved in 2 ml of dichloromethane and admixed with 27.9 mg (0.27 mmol) of triethylamine and 25.9 mg (0.25 mmol) of acetic anhydride. The solution is stirred at RT for three hours, taken up in ethyl acetate and washed once with water, and the aqueous phase is extracted once with ethyl acetate. The combined organic phases are washed two more times with water, dried with magnesium sulphate and concentrated using a rotary evaporator. Yield: 42.0 mg (50.8% of theory).

Rf (SiO$_2$, C1E2): 0.5.

Example 83

3-(5-Ethyl-4-(methylsulphinyl)-pyrimidin-2-yl)-1-(2-fluorobenzyl)-1H-pyrazolo[3,4-b]pyridine and 3-(5-Ethyl-4-(methylsulphonyl)pyrimidin-2-yl)-1-(2-fluorobenzyl)-1H-pyrazolo[3,4-b]pyridine

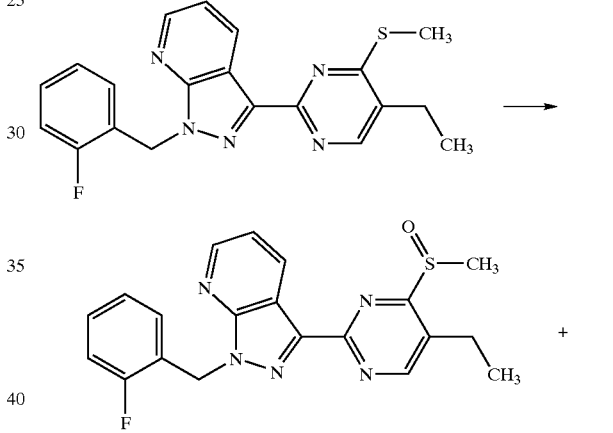

45.2 mg (0.12 mmol) of the methyl thioether (prepared from the chlorocompound used in Example 60 by reaction with sodium methanethiolate in toluene) and 30.8 mg (0.18 mmol) of MCPBA are stirred at 0° C. in 2 ml of dichloromethane. After three hours, the reaction mixture is admixed with sodium bicarbonate solution and ethyl acetate, separated, dried and concentrated using a rotary evaporator.

For purification, the substance is chromatographed over 8 g of silica gel 60 (particle size 0.040–0.063 mm) using cyclohexane/ethyl acetate 1:1 to 1:4 as mobile phase.

B: Yield: 36.0 mg (76.4% of theory). Rf (SiO$_2$, C1E2): 0.057 C: Yield: 7.1 mg (14.5% of theory). Rf (SiO$_2$, C1E2): 0.79.

Example 84

3-(4,6-Diamino-5-N-4-oxothiomorpholinopyrimidin-2-yl)-1-(2-fluorobenzyl)-1H-pyrazolo[3,4-b]pyridine and 3-(4,6-Diamino-5-N-4,4-dioxothiomorpholinopyrimidin-2-yl)-1-(2-fluorobenzyl)-1H-pyrazolo[3,4-b]pyridine

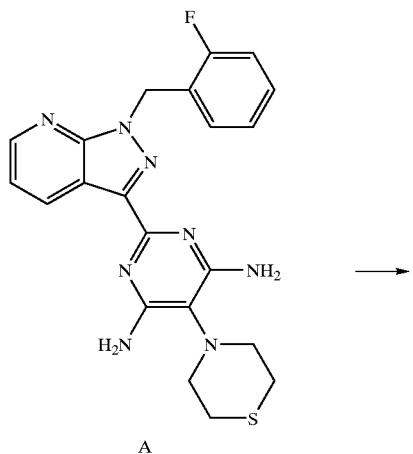

A

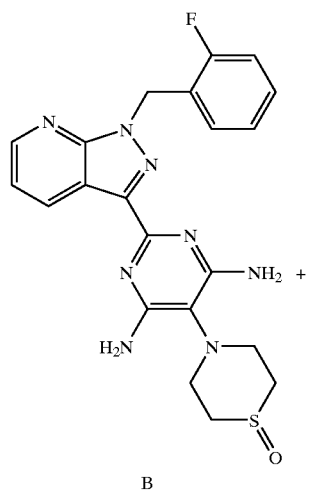

B

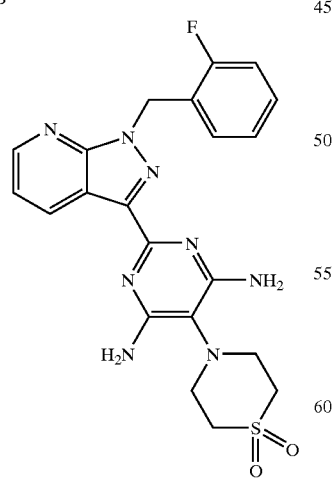

230 mg (0.53 mmol) of the thiomorpholine from Example 23 and 130 mg (0.53 mmol) of MCPBA are stirred at 0° C. in 5 ml of dichloromethane. After 30 min. an identical amount of MPCBA is added. After 1.5 hours, the reaction mixture is mixed with silica gel and concentrated using a rotary evaporator. For purification, the substance is chromatographed over silica gel 60 (particle size 0.040–0.063 mm) using cyclohexane/ethyl acetate.

B: Yield: 86 mg (36.1% of theory). Rf (SiO$_2$, BABA): 0.18 C: Yield 14 mg (5.7% of theory). Rf (SiO$_2$, BABA): 0.41.

What is claimed is:

1. A compound of the formula (I)

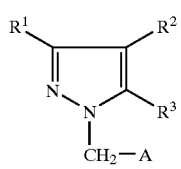

(I)

in which $R^1$ represents pyrimidinyl group, which is optionally substituted up to 2 times by identical or different radicals from the group (i) consisting of hydrogen, amino, azido, formyl, mercaptyl, carboxyl, hydroxyl, straight-chain or branched acyl, alkoxy, alkylthio or alkoxycarbonyl having in each case up to 6 carbon atoms, nitro, cyano, halogen, phenyl or straight-chain or branched alkyl having up to 6 carbon atoms which for its part may be substituted by hydroxyl, amino, azido, carboxyl, straight-chain or branched acyl, alkoxy, alkoxycarbonyl or acylamino having in each case up to 5 carbon atoms or by a radical of the formula —OR$^4$ in which $R^4$ represents straight-chain or branched acyl having up to 5 carbon atoms and/or is substituted by a radical of the formula

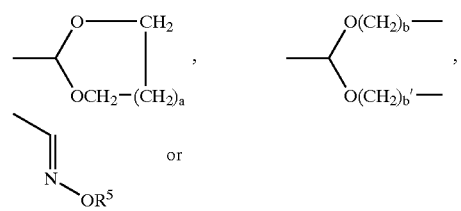

—S(O)$_c$—NR$^6$R$^7$ in which a, b and b' are identical or different and each represents a number 0, 1, 2 or 3, R⁵ is hydrogen or straight-chain or branched alkyl having up to 4 carbon atoms, c is a number 1 or 2 and R⁶ and R⁷ are identical or different and each represents hydrogen or straight-chain or branched alkyl having up to 10 carbon atoms which is optionally substituted by cycloalkyl having 3 to 8 carbon atoms or by aryl having 6 to 10 carbon atoms which for its part may be substituted by halogen, or represents aryl having 6 to 10 carbon atoms which is optionally substituted by halogen, or represents cycloalkyl having 3 to 7 carbon atoms, or R⁶ and R⁷ together with the nitrogen atom form a 5- to 7-membered saturated heterocycle which may optionally contain a further oxygen atom or a radical —NR⁸ in which

R⁸ represents hydrogen, straight-chain or branched alkyl having up to 4 carbon atoms or a radical of the formula

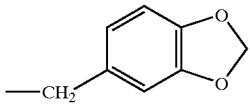

or benzyl or phenyl where the ring systems are optionally substituted by halogen, and which is substituted by at least one radical selected from the group (ii) consisting of imidazolyl, imidazolinyl, imidazolidinyl, morpholinyl, piperidinyl, piperazinyl, pyrrolidinyl, triazolyl, pyrrolyl, thiomorpholinyl, S-oxothiomorpholinyl, S,S-dioxothiomorpholinyl, thiazolyl, and thiadiazolyl, and which is optionally mono- or polysubstituted by a 5- or 6-membered ring which contains two oxygen atoms as ring members and forms a bicyclic unit or a spiro unit with the ring to which it is attached, and/or by hydroxyl, cyano, straight-chain or branched alkyl, acyl or alkoxycarbonyl having in each case up to 6 carbon atoms, where alkyl, acyl and alkoxycarbonyl may be substituted by hydroxyl, amino, halogen, carboxyl, straight-chain or branched acyl, alkoxy, alkoxycarbonyl or acylamino having in each case up to 5 carbon atoms, and an aryl ring having 6 to 10 carbon atoms which is substituted by straight-chain or branched alkyl having up to 4 carbon atoms, and $(C_2-C_{10})$alkenyl, $(C_2-C_{10})$alkinyl, $(C_7-C_{20})$alkyl, which is optionally substituted by aryl, halogen, cyano, dialkylamino, cycloalkyl, alkylamine, hydroxyl, amino, azido, carboxyl, straight-chain or branched acyl, alkoxy, alkoxycarbonyl or acylamino having in each case up to 5 carbon atoms or by a radical of the formula —OR⁴ in which

R⁴ represents straight-chain or branched acyl having up to 5 carbon atoms and $(C_1-C_6)$alkyl which is substituted 1- to 3 times by aryl, halogen(s), cyano, dialkylamino, alkylamino or cycloalkyl and acyl, which is substituted by halogen, acyloxy, or arylthio, and —NO or radicals of the formulae —SO₃H and —S(O)_d R⁹, in which d represents a number 1 or 2, R⁹ represents straight-chain or branched alkyl having 1 to 10 carbon atoms, cycloalkyl having 3 to 8 carbon atoms, aryl having 6 to 10 carbon atoms or thienyl, where the ring systems may optionally be substituted by halogen or by straight-chain or branched alkyl or alkoxy having in each case up to 4 carbon atoms, and a radical of the formula PO(OR¹⁰)(OR¹¹)

in which

R¹⁰ and R¹¹ are identical or different and each represents hydrogen, straight-chain or branched alkyl having up to 8 carbon atoms or cycloalkyl having 3 to 8 carbon atoms, aryl having 6 to 10 carbon atoms or benzyl, and oxycycloalkyl having 3 to 8 ring members or radicals of the formulae —CON═C(NH₂)₂, —C═NH (NH₂), —NH—C(═NH)NH₂ or (CO)ₑNR¹²R¹³ in which e represents a number 0 or 1,

R¹² and R¹³ are identical or different and each represents hydrogen, straight-chain or branched alkyl having up to 14 carbon atoms or cycloalkyl having 3 to 14 carbon atoms, or aryl having 6 to 10 carbon atoms, where the abovementioned radicals may optionally be substituted by aryl having 6 to 10 carbon atoms, cycloalkyl having 3 to 7 carbon atoms, hydroxyl, amino or straight-chain or branched alkoxy, acyl or alkoxycarbonyl having in each case up to 6 carbon atoms, and, in the case that e=1, R¹² and R¹³, together with the nitrogen atom to which they are attached, may also form a morpholinyl, pyrrolidinyl, or piperidinyl group, which may optionally be substituted up to 3 times by hydroxyl, alkoxy or alkyl having in each case up to 8 carbon atoms, and, in the case that e=0, R¹² and R¹³ may also represent straight-chain, branched or cyclic acyl having up to 14 carbon atoms, hydroxyalkyl, straight-chain or branched alkoxycarbonyl or acyloxyalkyl having in each case up to 6 carbon atoms, or a radical of the formula —SO₂R¹⁴ in which

R¹⁴ represents straight-chain or branched alkyl having up to 4 carbon atoms, and/or R¹² and R¹³ also represent radicals of the formulae

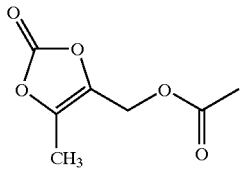

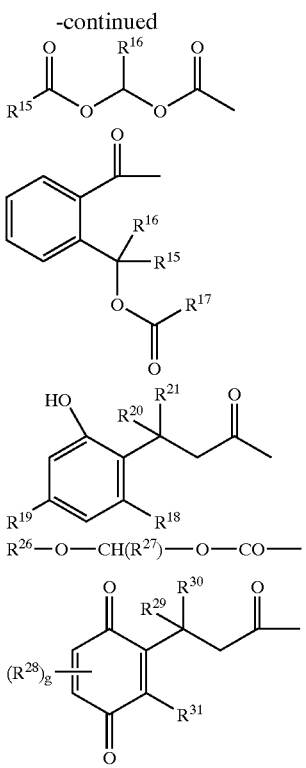

in which
R$^{15}$–R$^{16}$ and R$^{18}$–R$^{31}$ are identical or different and each represents hydrogen or straight-chain or branched alkyl having up to 4 carbon atoms,
g represents a number 0, 1 or 2,
and
R$^{17}$ represents phenyl, straight-chain or branched alkyl having up to 6 carbon atoms or cycloalkyl having 3 to 8 carbon atoms,
with the proviso that, if e=0, R$^{12}$ and R$^{13}$ do not simultaneously represent hydrogen, or R$^1$ represents a purine radical which may optionally be substituted up to three times by halogen, azido, cyano, hydroxyl, amino, monoalkylamino having up to 5 carbon atoms, dialkylamino having in each case up to 5 carbon atoms, alkyl having up to 5 carbon atoms and/or alkoxy having up to 5 carbon atoms, R$^2$ and R$^3$, together with the double bond, form a fused pyridyl ring, which is optionally substituted up to three times by identical or different substituents from the group consisting of formyl, carboxyl, hydroxyl, mercaptyl, straight-chain or branched acyl, alkylthio or alkoxycarbonyl having in each case up to 6 carbon atoms, nitro, cyano, halogen or straight-chain or branched alkyl or alkoxy having in each case up to 6 carbon atoms which for its part may be substituted by hydroxyl, amino, carboxyl, straight-chain or branched acyl, alkoxy or alkoxycarbonyl having in each case up to 5 carbon atoms,
and/or which is optionally substituted by a group of the formula —NR$^{32}$R$^{33}$
in which
R$^{32}$ and R$^{33}$ are identical or different and each represents hydrogen or straight-chain or branched alkyl having up to 6 carbon atoms, or
R$^{32}$ represents hydrogen and
R$^{33}$ represents acyl,
and/or which is optionally substituted by phenyl which for its part may be substituted up to 2 times by identical or different substituents from the group consisting of halogen and straight-chain or branched alkyl or alkoxy having in each case up to 6 carbon atoms,
and/or which is optionally substituted by a group of the formula —N=CH—NR$^{34}$R$^{35}$
in which
R$^{34}$ and R$^{35}$ are identical or different and each represents hydrogen, phenyl or straight-chain or branched alkyl having up to 6 carbon atoms,
A represents thienyl tetrahydropyranyl, tetrahydrofuranyl, phenyl, morpholinyl, pyrimidyl, pyrazinyl, pyridazinyl or pyridyl which are optionally substituted up to 3 times by identical or different substituents from the group consisting of amino, mercaptyl, hydroxyl, formyl, carboxyl, straight-chain or branched acyl, alkylthio, alkyloxyacyl, alkoxy or alkoxycarbonyl having in each case up to 6 carbon atoms, nitro, cyano, trifluoromethyl, azido, halogen, phenyl or straight-chain or branched alkyl having up to 6 carbon atoms which for its part may be substituted by hydroxyl, carboxyl, straight-chain or branched acyl, alkoxy or alkoxycarbonyl having in each case up to 5 carbon atoms,
and/or is substituted by a group of the formula —(CO)$_h$—NR$^{36}$R$^{37}$
in which
h represents a number 0 or 1,
R$^{36}$ and R$^{37}$ are identical or different and each represents hydrogen, phenyl, benzyl or straight-chain or branched alkyl or acyl having in each case up to 5 carbon atoms,
or a stereoisomeric form or salt thereof.

2. The compound of formula (I) according to claim 1
in which
R$^1$ represents a pyrimidinyl group,
which is optionally substituted up to 2 times by identical or different radicals from the group (i) consisting of
hydrogen, amino, azido, formyl, mercaptyl, carboxyl, hydroxyl, straight-chain or branched acyl, alkoxy, alkylthio or alkoxycarbonyl having in each case up to 6 carbon atoms, nitro, cyano, halogen, phenyl or straight-chain or branched alkyl having up to 6 carbon atoms which for its part may be substituted by hydroxyl, amino, azido, carboxyl, straight-chain or branched acyl, alkoxy, alkoxycarbonyl or acylamino having in each case up to 5 carbon atoms or by a radical of the formula —OR$^4$
in which
R$^4$ represents straight-chain or branched acyl having up to 5 carbon atoms
and/or is substituted by a radical of the formula

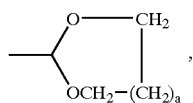 , 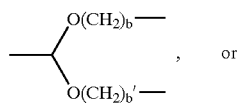 , or

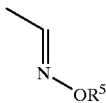

in which
a, b and b' are identical or different and each represents a number 0, 1, 2 or 3,
$R^5$ is hydrogen or straight-chain or branched alkyl having up to 4 carbon atoms, and which is substituted by at least one radical selected from the group (ii) consisting of
imidazolyl, imidazolinyl, imidazolidinyl, morpholinyl, piperidinyl, piperazinyl, pyrrolidinyl, triazolyl, pyrrolyl, thiomorpholinyl, S-oxothiomorpholinyl, S,S-dioxothiomorpholinyl, thiazolyl, and thiadiazolyl and which is optionally mono- or polysubstituted by a 5- or 6-membered ring which contains two oxygen atoms as ring members and forms a bicyclic unit or a spiro unit with the ring to which it is attached, and/or by hydroxyl, cyano, straight-chain or branched alkyl, acyl or alkoxycarbonyl having in each case up to 6 carbon atoms, where alkyl, acyl and alkoxycarbonyl may be substituted by hydroxyl, amino, halogen, carboxyl, straight-chain or branched acyl, alkoxy, alkoxycarbonyl or acylamino having in each case up to 5 carbon atoms, and
an aryl ring having 6 to 10 carbon atoms which is substituted by straight-chain or branched alkyl having up to 4 carbon atoms, and
($C_2$–C10)alkenyl, ($C_2$–$C_{10}$)alkynyl, ($C_7$–$C_{20}$)alkyl, which is optionally substituted by aryl, halogen, cyano, dialkylamino, cycloalkyl, alkylamine, hydroxyl, amino, azido, carboxyl, straight-chain or branched acyl, alkoxy, alkoxycarbonyl or acylamino having in each case up to 5 carbon atoms or by a radical of the formula —$OR^4$
in which
$R^4$ represents straight-chain or branched acyl having up to 5 carbon atoms and
($C_1$–$C_6$)alkyl which is substituted 1- to 3 times by aryl, halogen(s), cyano, dialkylamino, alkylamino or cycloalkyl and
acyl, which is substituted by halogen, or by acyloxy, or arylthio, and
—NO or radicals of the formulae —$SO_3H$ and —$S(O)_d R^9$,
in which
d represents a number 1 or 2,
$R^9$ represents straight-chain or branched alkyl having 1 to 10 carbon atoms, cycloalkyl having 3 to 8 carbon atoms, aryl having 6 to 10 carbon atoms or thienyl, where the ring systems may optionally be substituted by halogen or by straight-chain or branched alkyl or alkoxy having in each case up to 4 carbon atoms, and
a radical of the formula $PO(OR^{10})(OR^{11})$
in which
$R^{10}$ and $R^{11}$ are identical or different and each represents hydrogen, straight-chain or branched alkyl having up to 8 carbon atoms or cycloalkyl having 3 to 8 carbon atoms, aryl having 6 to 10 carbon atoms or benzyl, and
oxycycloalkyl having 3 to 8 ring members or radicals of the formulae —$CON=C(NH_2)_2$, —$C=NH(NH_2)$, —$NH—C(=NH)NH_2$ or $(CO)_e NR^{12}R^{13}$
in which
e represents a number 0 or 1,
$R^{12}$ and $R^{13}$ are identical or different and each represents hydrogen, straight-chain or branched alkyl having up to 14 carbon atoms or cycloalkyl having 3 to 14 carbon atoms, or aryl having 6 to 10 carbon atoms, where the abovementioned radicals may optionally be substituted by aryl having 6 to carbon atoms, cycloalkyl having 3 to 7 carbon atoms, hydroxyl, amino or straight-chain or branched alkoxy, acyl or alkoxycarbonyl having in each case up to 6 carbon atoms,
and, in the case that e=1,
$R^{12}$ and $R^{13}$, together with the nitrogen atom to which they are attached, may also form a piperidinyl, morpholinyl, or pyrrolidinyl group, which may optionally substituted up to 3 times by hydroxyl, alkoxy or alkyl having in each case up to 8 carbon atoms,
and, in the case that e=0,
$R^{12}$ and $R^{13}$ may also represent straight-chain, branched or cyclic acyl having up to 14 carbon atoms, hydroxyalkyl, straight-chain or branched alkoxycarbonyl or acyloxyalkyl having in each case up to 6 carbon atoms, or a radical of the formula —$SO_2R^{14}$
in which
$R^{14}$ represents straight-chain or branched alkyl having up to 4 carbon atoms,
and/or
$R^{12}$ and $R^{13}$ also represent radicals of the formulae

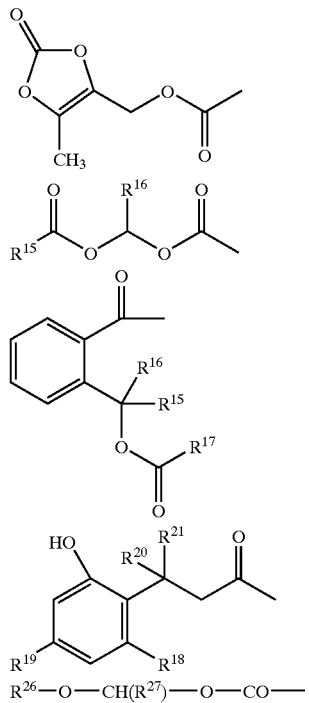

-continued

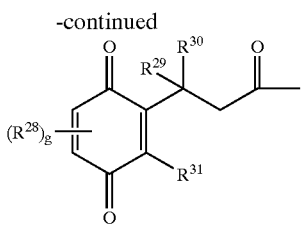

in which
R$^{15}$–R$^{16}$ and R$^{18}$–R$^{31}$ are identical or different and each represents hydrogen or straight-chain or branched alkyl having up to 4 carbon atoms,
g represents a number 0, 1 or 2,
and
R$^{17}$ represents phenyl, straight-chain or branched alkyl having up to 6 carbon atoms or cycloalkyl having 3 to 8 carbon atoms,
with the proviso that, if e=0, R$^{12}$ and R$^{13}$ do not simultaneously represent hydrogen,
or
R$^1$ represents a purine radical which may optionally be substituted up to three times by halogen, azido, cyano, hydroxyl, amino, monoalkylamino having up to 5 carbon atoms, dialkylamino having in each case up to 5 carbon atoms, alkyl having up to 5 carbon atoms and/or alkoxy having up to 5 carbon atoms,
R$^2$ and R$^3$, together with the double bond, form a fused pyridyl ring,
which is optionally substituted up to 2 times by identical or different substituents from the group consisting of formyl, carboxyl, hydroxyl, mercaptyl, straight-chain or branched acyl, alkylthio or alkoxycarbonyl having in each case up to 5 carbon atoms, nitro, cyano, azido, fluorine, chlorine, bromine or straight-chain or branched alkyl or alkoxy having in each case up to 5 carbon atoms which for its part may be substituted by hydroxyl, amino, carboxyl, straight-chain or branched acyl, alkoxy or alkoxycarbonyl having in each case up to 4 carbon atoms,
and/or
the abovementioned fused pyridyl ring is optionally substituted by a group of the formula —NR$^{32}$R$^{33}$
in which
R$^{32}$ and R$^{33}$ are identical or different and represent hydrogen or straight-chain or branched alkyl having up to 4 carbon atoms
or
R$^{32}$ represents hydrogen
and
R$^{33}$ represents formyl
and/or the abovementioned fused pyridyl ring is optionally substituted by phenyl which for its part may be substituted by fluorine, chlorine, bromine or by straight-chain or branched alkyl or alkoxy having in each case up to 4 carbon atoms,
A represents thienyl, tetrahydropyranyl, tetrahydrofuranyl, phenyl, morpholinyl, pyrimidyl, pyrazinyl, pyridazinyl or pyridyl which are optionally substituted up to 2 times by identical or different substituents from the group consisting of hydroxyl, formyl, carboxyl, straight-chain or branched acyl, alkylthio, alkyloxyacyl, alkoxy or alkoxycarbonyl having in each case up to 4 carbon atoms, fluorine, chlorine and bromine,
or a stereoisomeric form or salt thereof.

3. The compound of formula (I) according to claim 1 in which

R$^1$ represents a pyrimidinyl group
which is optionally substituted up to 2 times by identical or different radicals from the group (i) consisting of
hydrogen, amino, hydroxyl, alkoxy or alkoxycarbonyl having in each case up to 3 carbon atoms, cyano or halogen,
and which is substituted by at least one radical selected from the group (ii) consisting of
imidazolyl, imidazolinyl, imidazolidinyl, morpholinyl, piperidinyl, piperazinyl, pyrrolidinyl, triazolyl, pyrrolyl and thiomorpholinyl and which is optionally mono- or polysubstituted by a 5-membered ring which contains two oxygen atoms as ring members and which forms, with the ring to which it is attached, a bicyclic unit or a spiro unit, and/or by hydroxyl, cyano, straight-chain or branched alkyl, acyl or alkoxycarbonyl having in each case up to 3 carbon atoms, where alkyl, acyl and alkoxycarbonyl may be substituted by hydroxyl, amino, halogen, carboxyl, straight-chain or branched acyl or alkoxy having in each case up to 3 carbon atoms,
and
a tolyl radical,
and
C$_7$-alkyl which is optionally substituted by cyano,
and
(C$_1$–C$_5$)alkyl, which is 1- to 3-times substituted by halogen(s), cyano, or aryl,
and
—NO or radicals of the formula —S(O)$_d$R$^9$,
in which
d represents a number 1 or 2,
R$^9$ represents straight-chain or branched alkyl having 1 to 4 carbon atoms, aryl having 6 carbon atoms or thienyl,
and
a radical of the formula PO(OR$^{10}$)(OR$^{11}$),
in which
R$^{10}$ and R$^{11}$ are identical or different and each represents straight-chain or branched alkyl having up to 3 carbon atoms,
and
radicals of the formulae —NH—C(=NH)NH$_2$ and or (CO)$_e$NR$^{12}$R$^{13}$
in which
e represents a number 0 or 1,
R$^{12}$ and R$^{13}$ are identical or different and each represents hydrogen, straight-chain or branched alkyl having up to 4 carbon atoms or cycloalkyl having 3 carbon atoms, where the abovementioned radicals may optionally be substituted by aryl having 6 carbon atoms, furyl, cycloalkyl having 3 carbon atoms, hydroxyl, straight-chain alkoxy having up to 2 carbon atoms,
and, in the case that e=1,
R$^{12}$ and R$^{13}$, together with the nitrogen atom to which they are attached, may also form a piperidinyl, morpholinyl, or pyrrolidinyl group which may optionally be substituted up to 2 times by hydroxyl or methyl,
and, in the case that e=0, $R^{12}$ and $R^{13}$ may also represent straight-chain acyl having up to 14 carbon atoms, and/or $R^{12}$ and $R^{13}$ also represent a radical of the formula

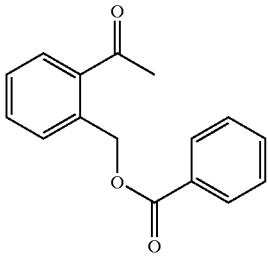

with the proviso that in the case that e=0, $R^{12}$ and $R^{13}$ do not simultaneously represent hydrogen, or $R^1$ represents a purine radical which may optionally be substituted up to two times by halogen, azido, amino, monoalkylamino having up to 4 carbon atoms and/or methyl, $R^2$ and $R^3$ together with the double bond form a fused pyridyl ring, A represents phenyl or pyrimidyl, which are optionally substituted by fluorine, chlorine or bromine, or a stereoisomeric form or salt thereof.

4. The compound according to claim 1, where $R^1$ represents a radical of the formula

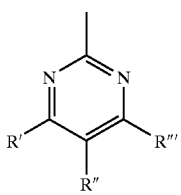

in which

R' represents $NH_2$,

R" represents optionally substituted morpholinyl, piperidinyl, piperazinyl, pyrrolidinyl, triazolyl or thiomorpholinyl and R'" represents hydrogen or $NH_2$.

5. Compounds according to claim 4 in which R" represents morpholinyl.

6. A process for preparing compounds of formula (I) of claim 1, characterized in that in the case that $R^1$ represents an optionally substituted pyrimidine radical, amidines of the formula (IX)

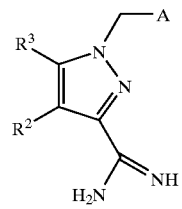

in which

A, $R^2$ and $R^3$ are each as defined above in claim 1, are reacted with compounds of the formula (X), (Xa), (Xb) or (Xc)

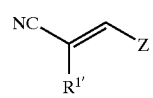

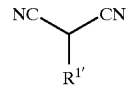

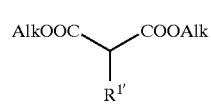

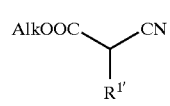

in which $R^{1'}$ represents the optionally substituted cycloalkyl radical listed above under $R^1$;

Alk represents straight-chain or branched alkyl having up to 8 carbon atoms, and Z represents an $NH_2$ group, a monoalkylamino group having up to 7 carbon atoms, a dialkylamino group having up to 7 carbon atoms, a piperidinyl or morpholinyl radical which is attached via the nitrogen, hydroxyl, alkoxy having up to 7 carbon atoms, acyloxy having up to 7 carbon atoms or aroyloxy having 6 to 10 carbon atoms, and, in the case of the groups $—S(O)_c NR^6 R^7$ and $—S(O)_{c'} NR^{6'}R^{7'}$, starting from the unsubstituted compounds of the formula (1), reacted initially with thionyl chloride and, in a second step, with the appropriate amines and the substituents listed under X, Y, $R^1$, $R^2$, $R^3$ and/or $R^4$ are modified or introduced by acylation of free amino groups or hydroxyl groups, chlorination, catalytic, hydrogenation, reduction, oxidation, removal of protective groups and/or nucleophilic substitution.

7. A pharmaceutical composition comprising a compound of formula (I) according to claim 1 and a pharmaceutically acceptable carrier.

8. A method of treating the cardiovascular disease hypertension comprising administering to a mammal an effective amount of a compound according to claim 1.

* * * * *